US010004473B2

(12) United States Patent
Tsai et al.

(10) Patent No.: US 10,004,473 B2
(45) Date of Patent: Jun. 26, 2018

(54) HEART RATE DETECTION METHOD AND DEVICE USING HEART SOUND ACQUIRED FROM AUSCULTATION POSITIONS

(71) Applicant: IMEDIPLUS INC., Chupei, Hsinchu County (TW)

(72) Inventors: Kun-Hsi Tsai, Chupei (TW); Shih-I Yang, Chupei (TW); Shih-Hsuan Ku, Chupei (TW); Tzu-Chen Liang, Chupei (TW); Lei Wan, Taichung (TW); Chung Lun Chen, Taichung (TW); Wen Ling Liao, Taichung (TW); Yu Hsuan Chen, Taipei (TW)

(73) Assignee: IMEDIPLUS INC., Chupei (TW)

( * ) Notice: Subject to any disclaimer, the term of this patent is extended or adjusted under 35 U.S.C. 154(b) by 348 days.

(21) Appl. No.: 14/849,619

(22) Filed: Sep. 10, 2015

(65) Prior Publication Data

US 2017/0071564 A1 Mar. 16, 2017

(51) Int. Cl.
| | |
|---|---|
| *A61B 7/04* | (2006.01) |
| *A61B 5/0205* | (2006.01) |
| *A61B 5/04* | (2006.01) |
| *A61B 5/0402* | (2006.01) |
| *A61B 5/0432* | (2006.01) |
| *A61B 5/046* | (2006.01) |
| *A61B 5/0464* | (2006.01) |
| *A61B 7/00* | (2006.01) |
| *A61B 5/024* | (2006.01) |
| *A61B 5/0245* | (2006.01) |
| *A61B 5/0255* | (2006.01) |
| *A61B 5/00* | (2006.01) |

(52) U.S. Cl.
CPC .............. *A61B 7/04* (2013.01); *A61B 5/0205* (2013.01); *A61B 5/0402* (2013.01); *A61B 5/046* (2013.01); *A61B 5/04017* (2013.01); *A61B 5/0432* (2013.01); *A61B 5/0464* (2013.01); *A61B 7/00* (2013.01); *A61B 5/0245* (2013.01); *A61B 5/0255* (2013.01); *A61B 5/02438* (2013.01); *A61B 5/725* (2013.01); *A61B 2505/01* (2013.01)

(58) Field of Classification Search
CPC .......... A61B 7/00; A61B 7/04; A61B 5/04017
See application file for complete search history.

(56) References Cited

U.S. PATENT DOCUMENTS

2004/0260188 A1* 12/2004 Syed .................... A61B 5/0456
600/509

\* cited by examiner

*Primary Examiner* — Alyssa M Alter
(74) *Attorney, Agent, or Firm* — Chieh-Mei Wang

(57) ABSTRACT

A heart rate detection method for calculating heart rate using heart sound from auscultation positions identified by a statistical approach utilizes a down-sampling and filtering process to acquire samples of heart sound from multiple auscultation positions of multiple testees and calculate heart rate with the samples, records time for calculating heart rate from each auscultation position of each testee and record the same from electrocardiogram, calculates a mean error and a standard deviation of the time to identify the auscultation positions allowing faster speed in heart rate detection, and applies a Bland-Altman difference plot and both a coefficient of determination and a Pearson's correlation coefficient to determine the degree of consistency and correlation of the heart rate measured from the multiple auscultation positions to identify the auscultation positions allowing generation of precise heart rate.

10 Claims, 34 Drawing Sheets

HEART RATE DETECTION METHOD AND DEVICE USING HEART SOUND ACQUIRED FROM AUSCULTATION POSITIONS

BACKGROUND OF THE INVENTION

1. Field of the Invention

The present invention relates to a heart rate detection method and, more particularly, to a hear rate calculation method for calculating heart rate with heart sound samples at a reduced frequency and identifying the auscultation positions that generate the heart sound for calculating the heart rate having the performance and correlation close to heart rate calculated through electrocardiography.

2. Description of the Related Art

Heart rate is one of the vital signs used to measure the body's basic function and is essential to clinicians' access to patient treatment and evaluation of patient's status. Electrocardiogram (ECG) and phonocardiogram (PCG) can both used to measure heart rate. ECG differs from PCG in that ECG records the electrical activities of the heart while PCG records the sounds the heart produces. Compared to ECG, PCG diagnosis is much easier by placing the stethoscope against one of the auscultation positions.

When experiencing a critical condition, such as pulseless electronic activity (PEA) that is a clinical condition characterized by unresponsiveness and lack of palpable pulse in the presence of cardiac rhythm while can be observed on ECG, the phenomenon of ECG oftentimes leads to misjudgment in diagnosing the critical condition.

In the event of a cardiac emergency caused by cardiovascular diseases, the patient or the wounded person may lose the best chance of saving their lives due to misjudgment, inappropriate first aid measures or long judgment time. How to quickly prepare equipment and position a probe on the patient to collect sufficient data for calculating the heart rate within a short period of time is always one of the top concerns on the list. Currently, a common way of measuring heart rate of a patient or a wounded person is to apply a pulse oximeter to a fingertip of the patient or the wounded person to measure oxygen concentration and transform the oxygen concentration into heart rate, which is very unstable and can be influenced by injured limb or nail decoration, such as nail polish, nail art, and the like.

To cope with the infeasibility or inconvenience upon measuring heart rate at fingertip, an approach of measuring heart rate at other body locations instead of fingertip, which has good performance and acceptable correlation when benchmarking with the measurements of heart rate done by physiological monitors through the means of electrocardiogram (ECG), should be provided.

SUMMARY OF THE INVENTION

An objective of the present invention is to provide a heart rate detection method using heart sound acquired from auscultation positions, which reduces samples required for heart rate detection and identifies auscultation positions that generates heart sound required for fast calculation and high correlation relative to heart rate calculated through electrocardiography.

To achieve the foregoing objective, the heart rate detection method using heart sounds acquired from auscultation positions, wherein the heart rate detection method is built in a heart rate detection device and is performed by a processor of the heart rate detection device, the heart rate detection method has steps of:

repeatedly acquiring and processing samples of heart sound at a first sampling frequency from multiple auscultation positions of multiple testees using a heart sound identification and heart rate detection process to identify a first heart sound occurring at beginning of each systole and a second heart sound occurring at beginning of a diastole paired to the systole from the samples acquired at a second sampling frequency, wherein the multiple auscultation positions include an auscultation position for mitral valve, an auscultation position for pulmonary valve, a first auscultation position for aortic valve, a second auscultation position for aortic valve, and an auscultation position for tricuspid valve;

calculating a target heart rate for each auscultation position of each testee according to each pair of the first heart sound and the second heart sound, and recording a target heart rate detection time for the auscultation position of the testee when calculation of the target heart rate for the auscultation position of the testee is completed for the first time; and recording a reference heart rate for each auscultation position of each testee and a reference heart rate detection time for the auscultation position of the testee when calculation of the reference heart rate for the auscultation position is completed by a reference electrocardiogram (ECG) heart rate detector for the first time.

The target heart rate detection time, the reference heart rate detection time, the target heart rate and the reference heart rate for each auscultation position are analyzed by a statistical process to obtain an analysis result that the target heart rate detection time measured from the auscultation position for tricuspid valve, the auscultation position for pulmonary valve and the auscultation position for mitral valve is faster than the target heart rate measured from any other auscultation positions, the target heart rate detection time measured from the auscultation position for mitral valve and the auscultation position for tricuspid valve has higher degree of stability than the target heart rate detection time measured from any other auscultation positions, and the target heart rate measured from the tricuspid position and the mitral position is more accurate than the target heart rate measured from any other auscultation positions.

Given the foregoing heart rate detection method, samples or heart sound can be lowered from the first sampling frequency to the second sampling frequency, the statistical approach incorporating the use of mean error, standard deviation error, the Bland-Altman difference plot, the coefficient of determination and the Pearson's correlation coefficient to identify the auscultation positions ensuring generation of heart sound for faster calculation of precise heart rate with high degree of consistency and correlation.

Other objectives, advantages and novel features of the invention will become more apparent from the following detailed description when taken in conjunction with the accompanying drawings.

DETAILED DESCRIPTION OF THE INVENTION

Figure 1:
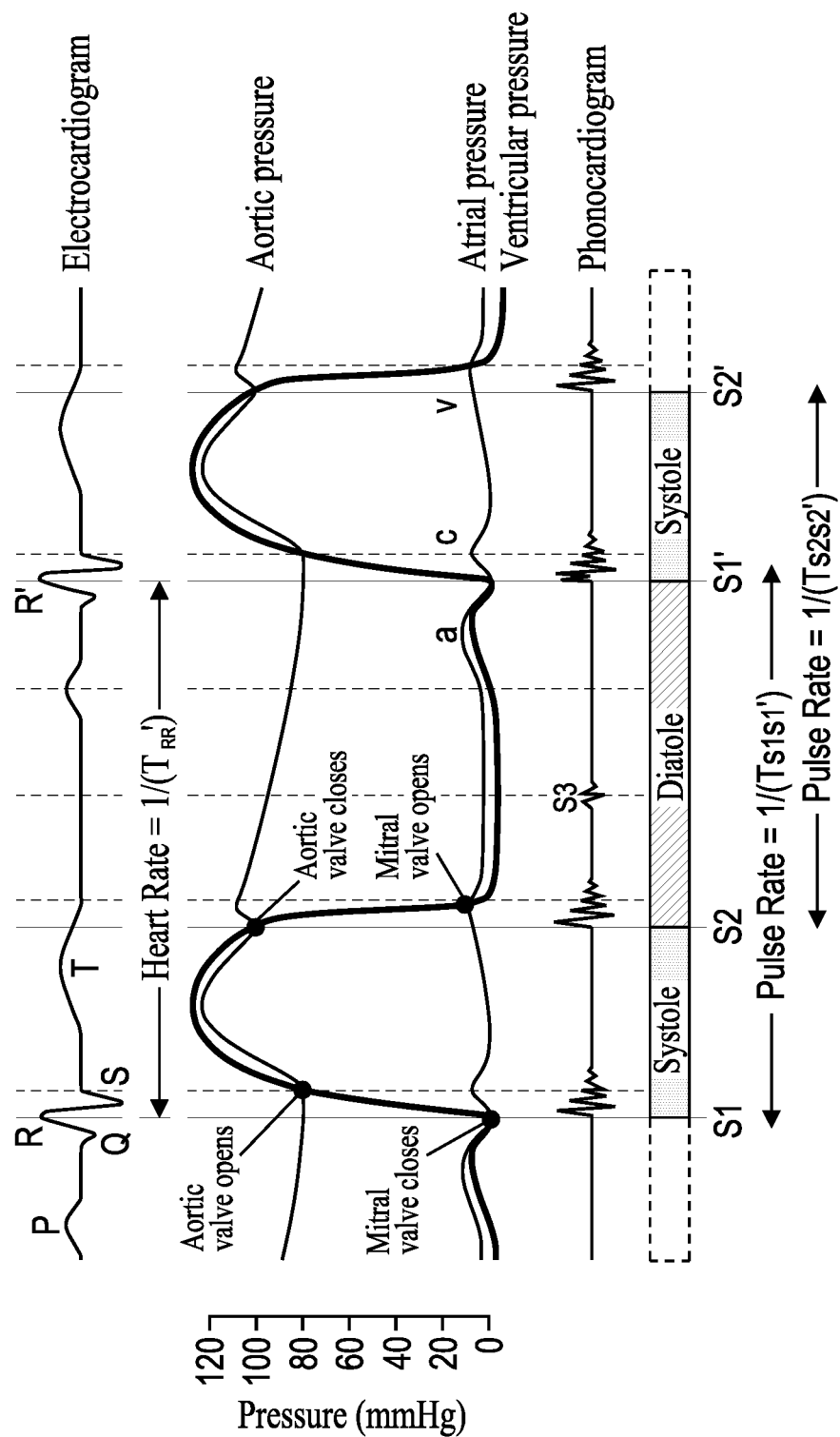
FIG. 1 is a graph illustrating curves for identifying pulse through ECG and PCG.

Basically, heart rate indicates the frequency of heart beat, which is the frequency of a cardiac cycle including a systole phase and a diastole phase, and heart sound is the sound uttered when heart is beating. With reference to FIG. 1, heart rate can be found and calculated by two approaches, namely, electrocardiogram (ECG) and phonocardiogram (PCG). A curve in the bottom representing the PCG approach shows the first heart sound (S1), which occurs at the beginning of each systole, and the second heart sound (S2), which occurs at the beginning of each diastole. According to ECG, the first heart sound (S1) can be interpreted as the timing when the mitral valve closes, and the second heart sound (S2) can be interpreted as the timing when the aortic valve closes. As can be seen from FIG. 1, a time duration between a first heart sound (S1) and a subsequent first heart sound (S1') in the PCG and a time duration between two successive pulses abruptly rising in a curve represented by ventricular pressure in the ECG correspond to each other and can be used to calculate the heart rate. This also explains why ECG and PCG can both be used to determine heart rate.

Figure 2:
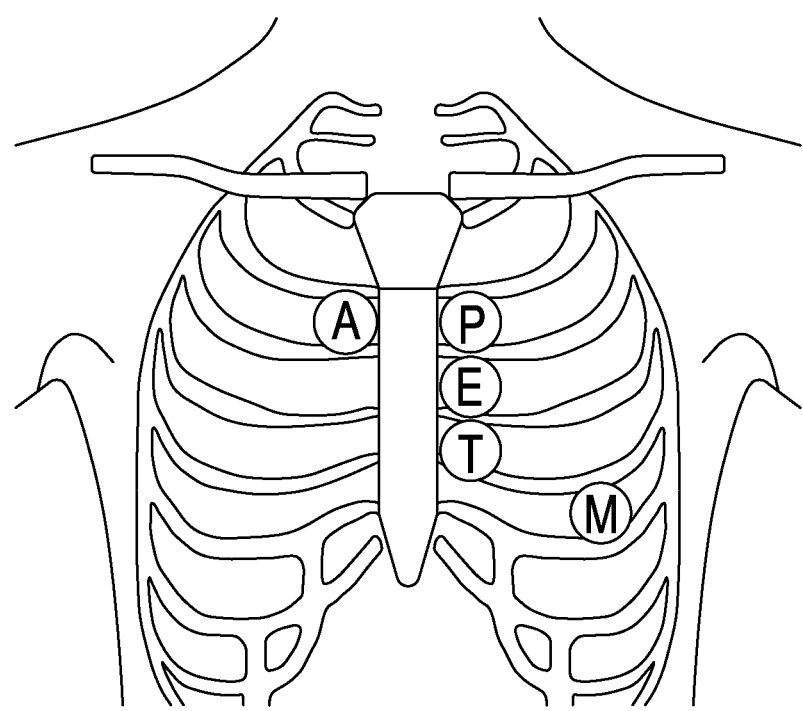
FIG. 2 is a schematic diagram illustrating auscultation positions of heart sound.

To perform adequate auscultation for the first heart sound (S1) and the second heart sound (S2), with reference to FIG. 2, the auscultation positions are preferred to correspond to the heart valves and are marked by 'M', 'P', 'A', 'T', and 'E'. The auscultation position 'M' represents the auscultation position for the mitral valve situated in the left fifth intercostals space (ICS) close to the midclavicular line (MCL). The auscultation position 'P' represents the auscultation position for the pulmonary valve situated in the left second ICS close to the parasternal line (PSL). The auscultation position 'A' represents the first auscultation position for aortic valve situated in the right second ICS close to the PSL. The auscultation position 'T' represents the auscultation position for tricuspid valve situated in the left fourth ICS close to the PSL. The auscultation position 'E' represents the auscultation position for Erb's point serving as the second auscultation position for aortic valve and situated in the left third ICS close to the PSL.

Figure 3:
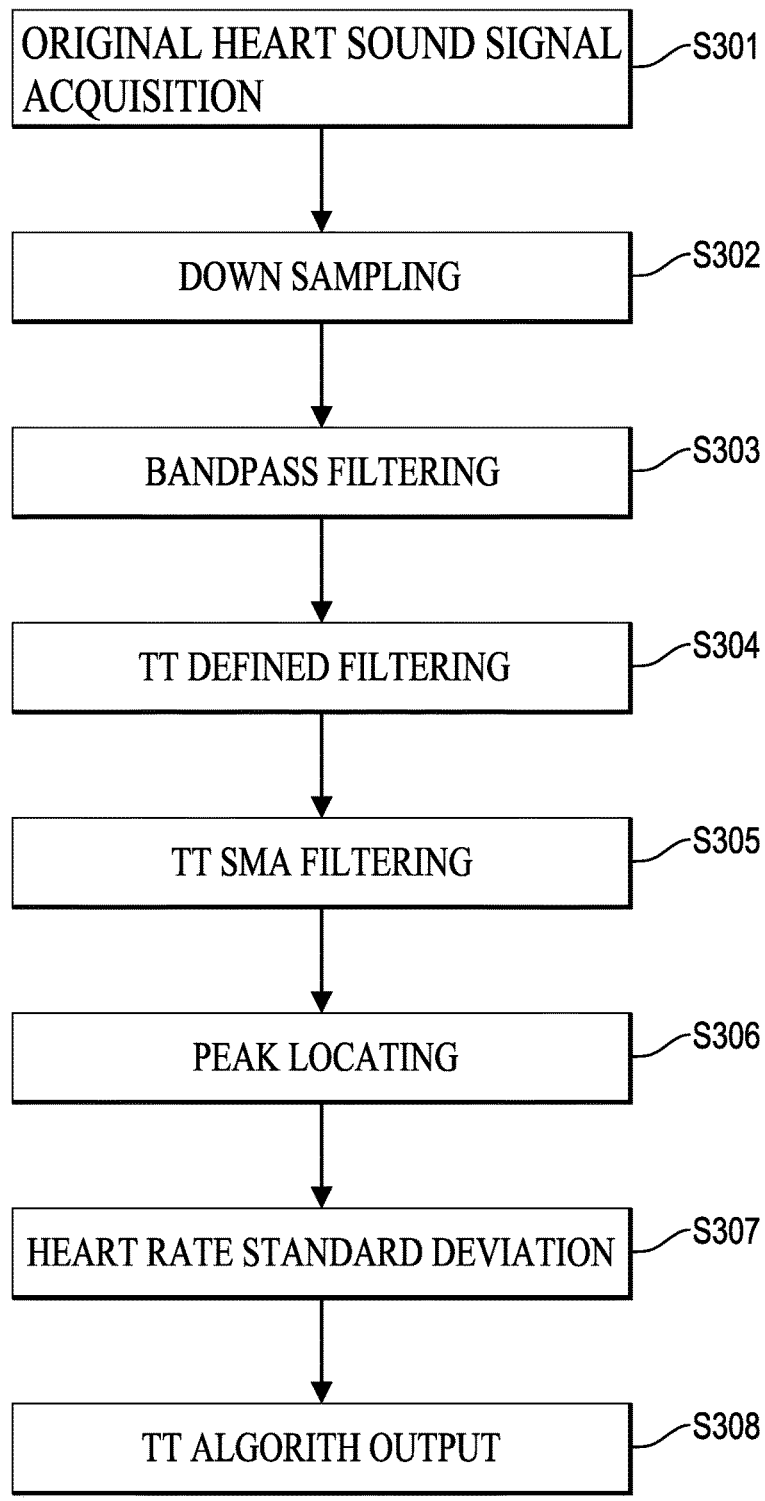
FIG. 3 is a flow diagram of a heart rate detection method in accordance with the present invention.

With reference to FIG. 3, a heart rate detection method using heart sound acquired from auscultation positions in accordance with the present invention has the following steps.

Figure 4:
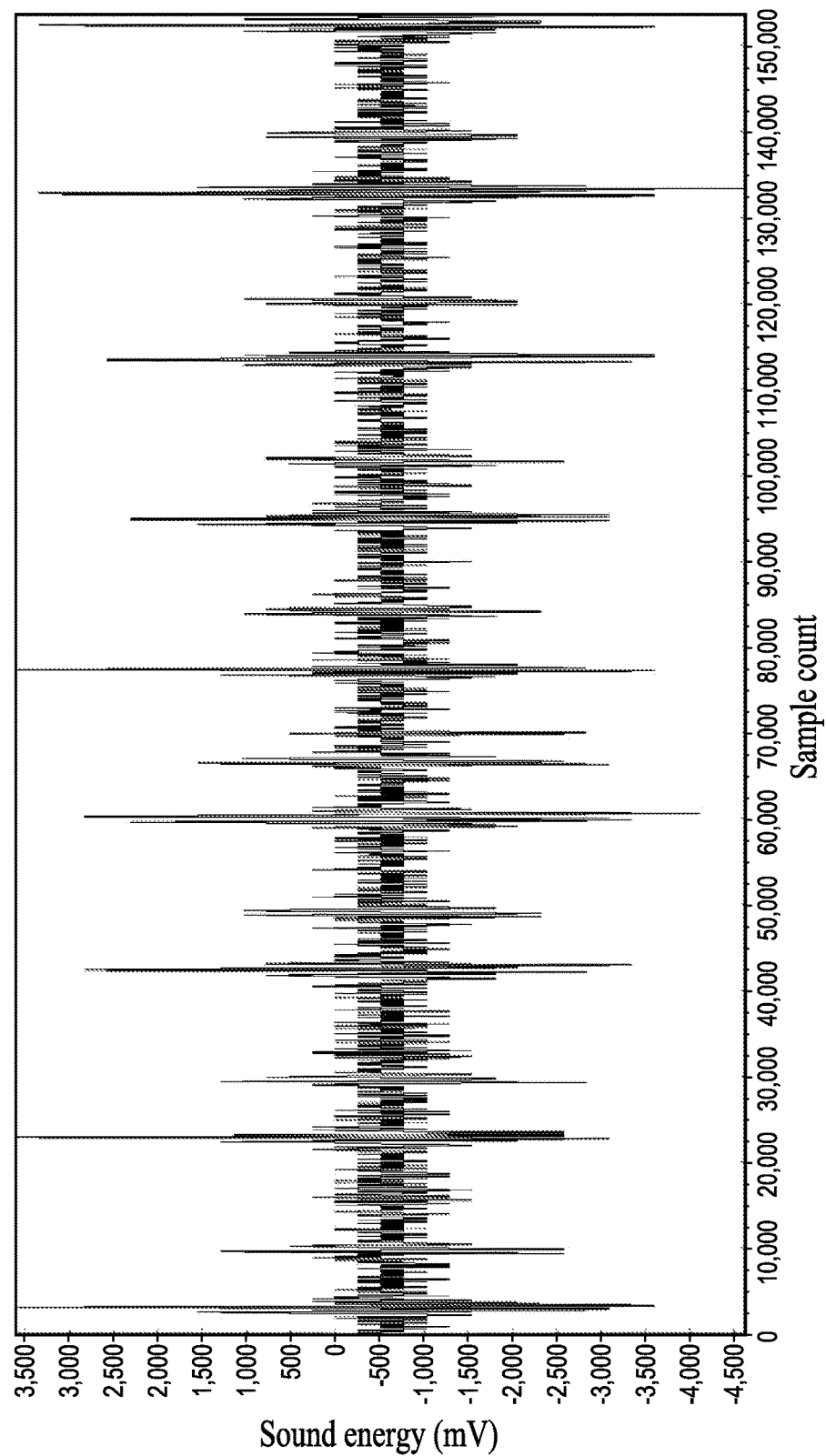
FIG. 4 is a curve diagram of original heart sound signals acquired by the original heart sound signals acquisition step in the heart rate detection method in FIG. 3.

Step S301: Original heart sound signal acquisition step. Specifically, sample heart sound signals from multiple auscultation positions of a person at a first sampling frequency. The first samples of heart sound signal are acquired by a sound pickup device. The first frequency is 48 kHz. With reference to FIG. 4, a curve representing the initial samples of heart sound signals acquired at the first sampling frequency is shown.

Figure 5:
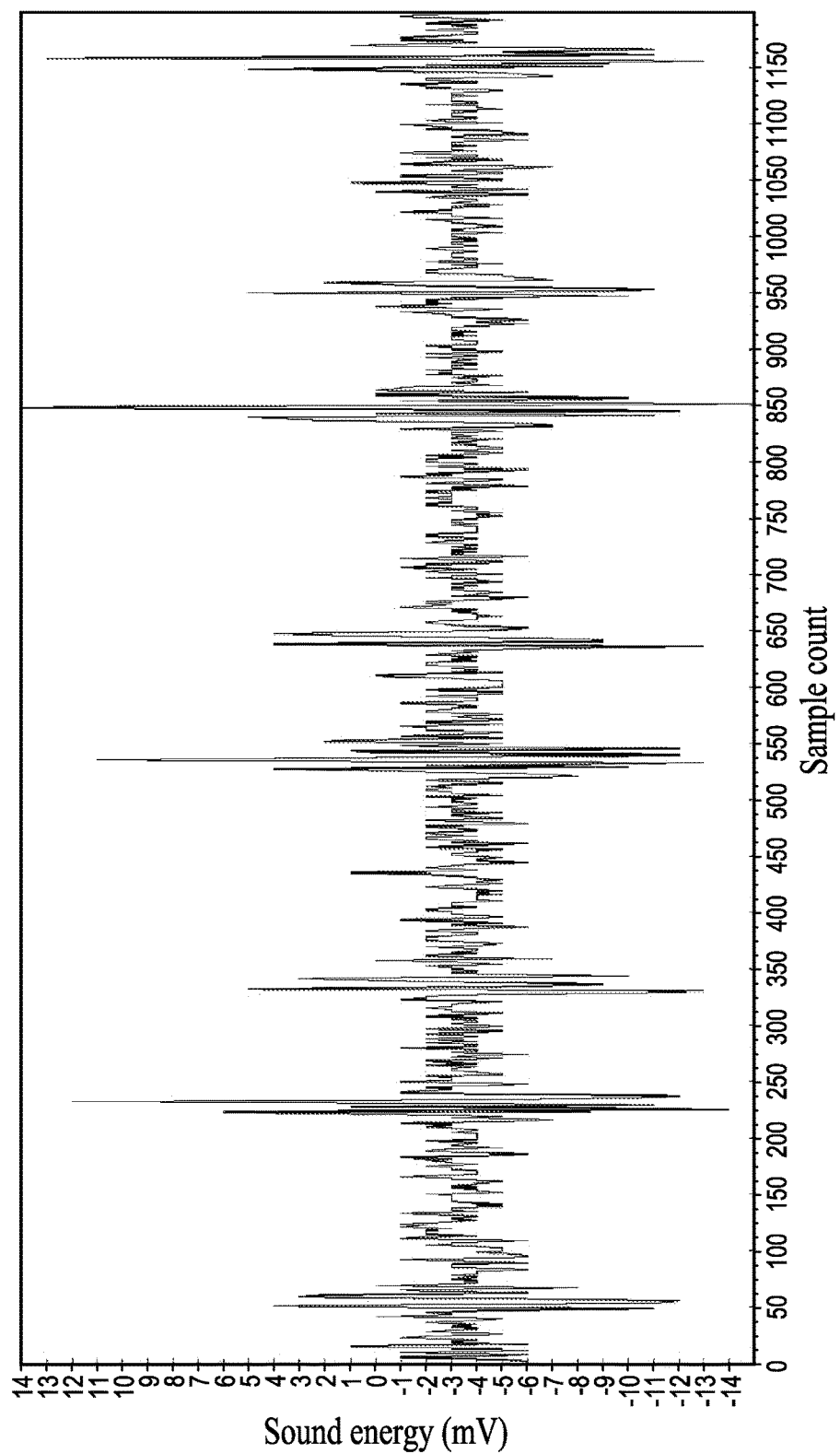
FIG. 5 is a curve diagram of heart sound signals done by a down-sampling step of the heart rate detection method in FIG. 3.
Figure 6:
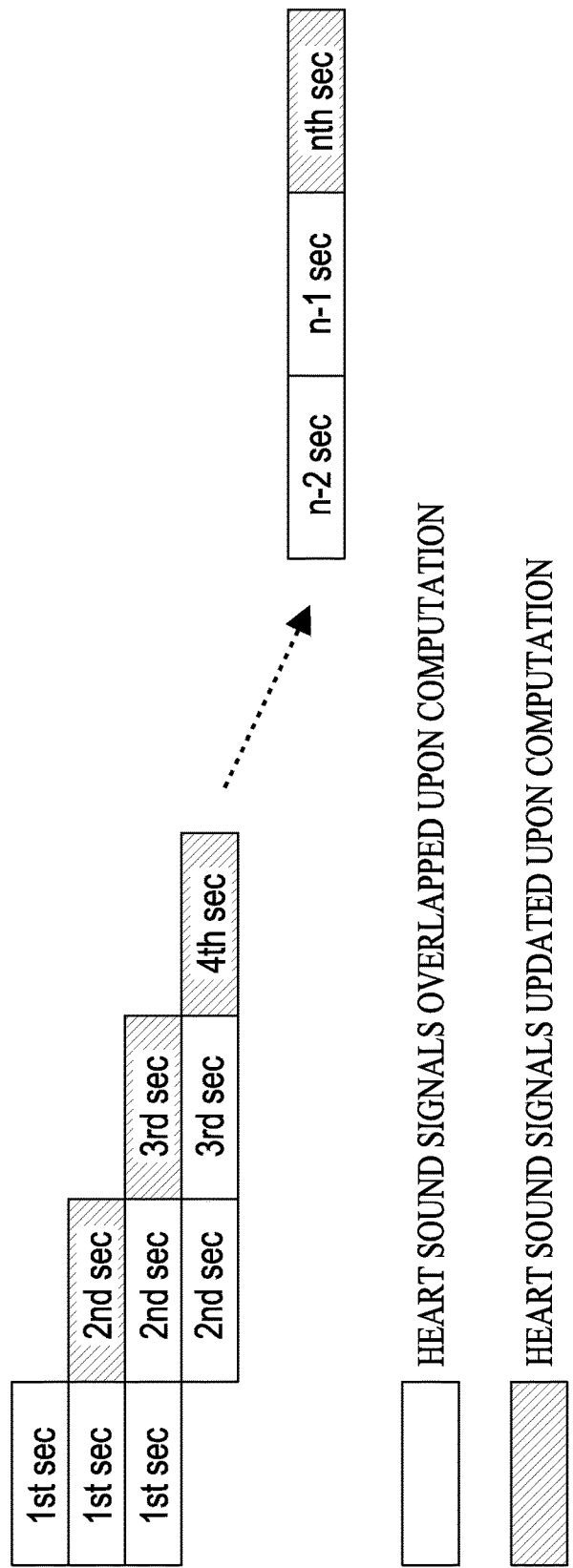
FIG. 6 is a timing diagram illustrating to overlap down-sampled heart sound signals for computation of heart rate.
Figure 7:
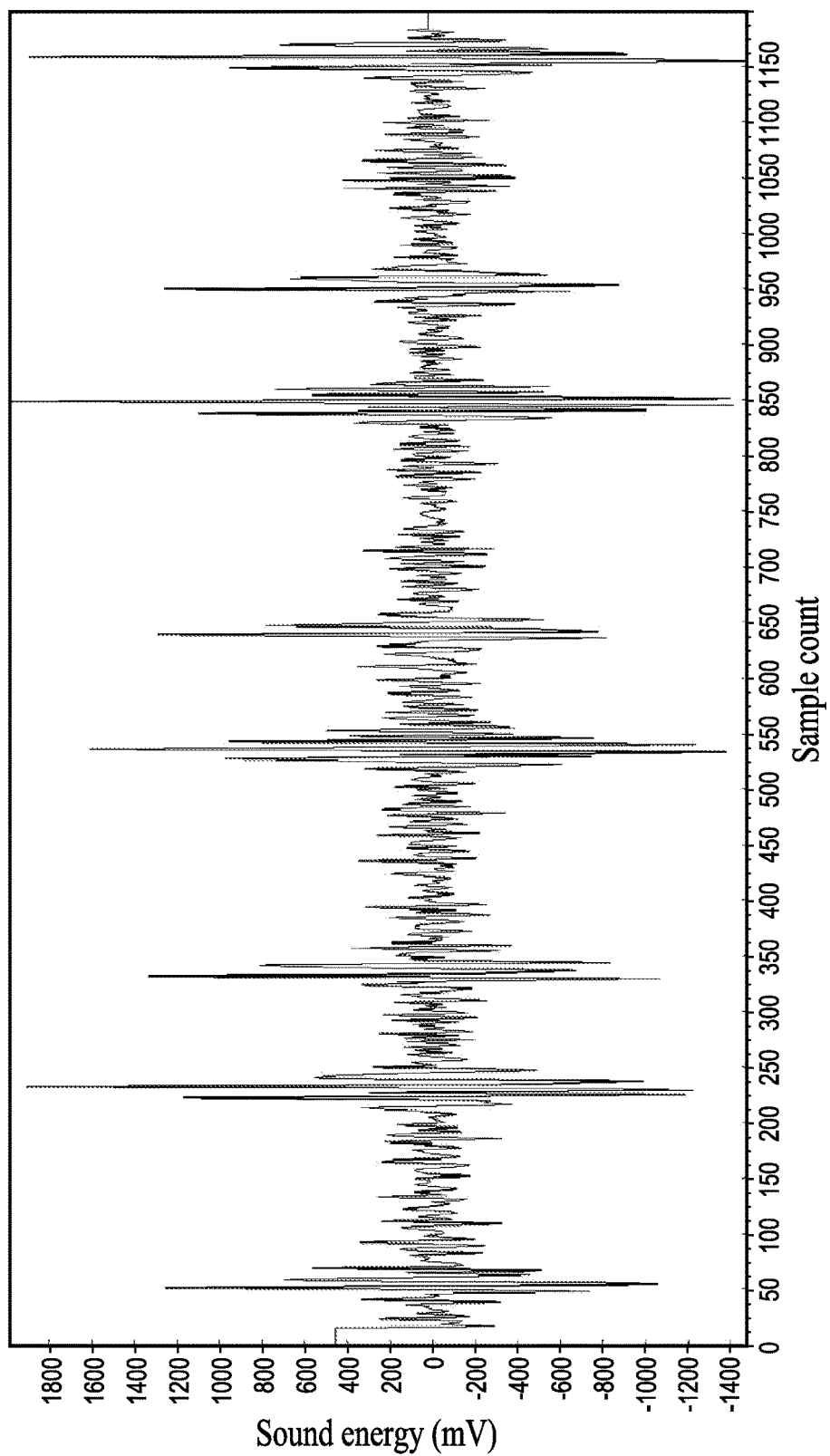
FIG. 7 is a curve diagram of heart sound signals done by a bandpass filtering step in FIG. 3.
Figure 8:
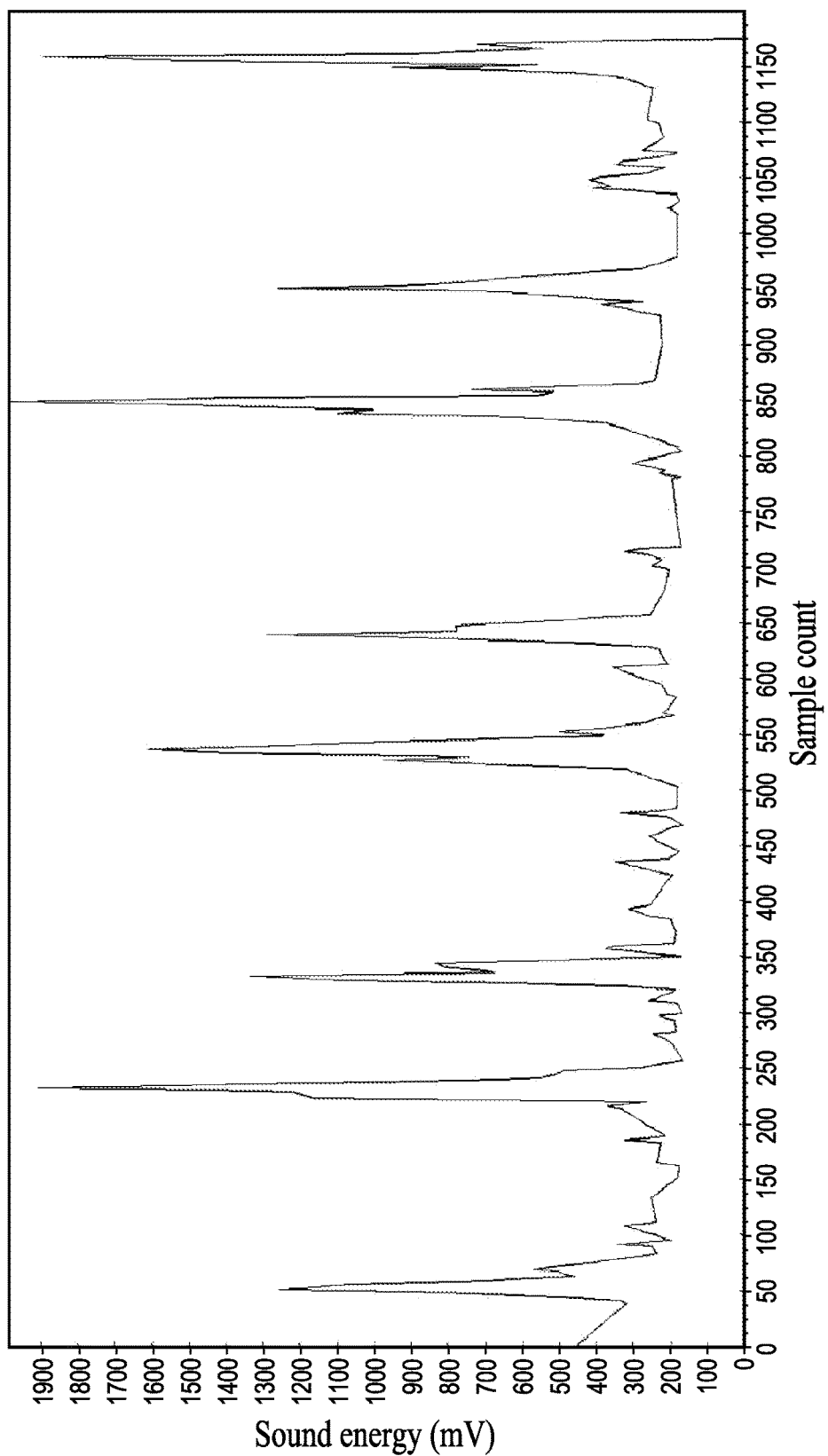
FIG. 8 is a curve diagram of heart sound signals done by a TT defined filtering step in FIG. 3.
Figure 9:
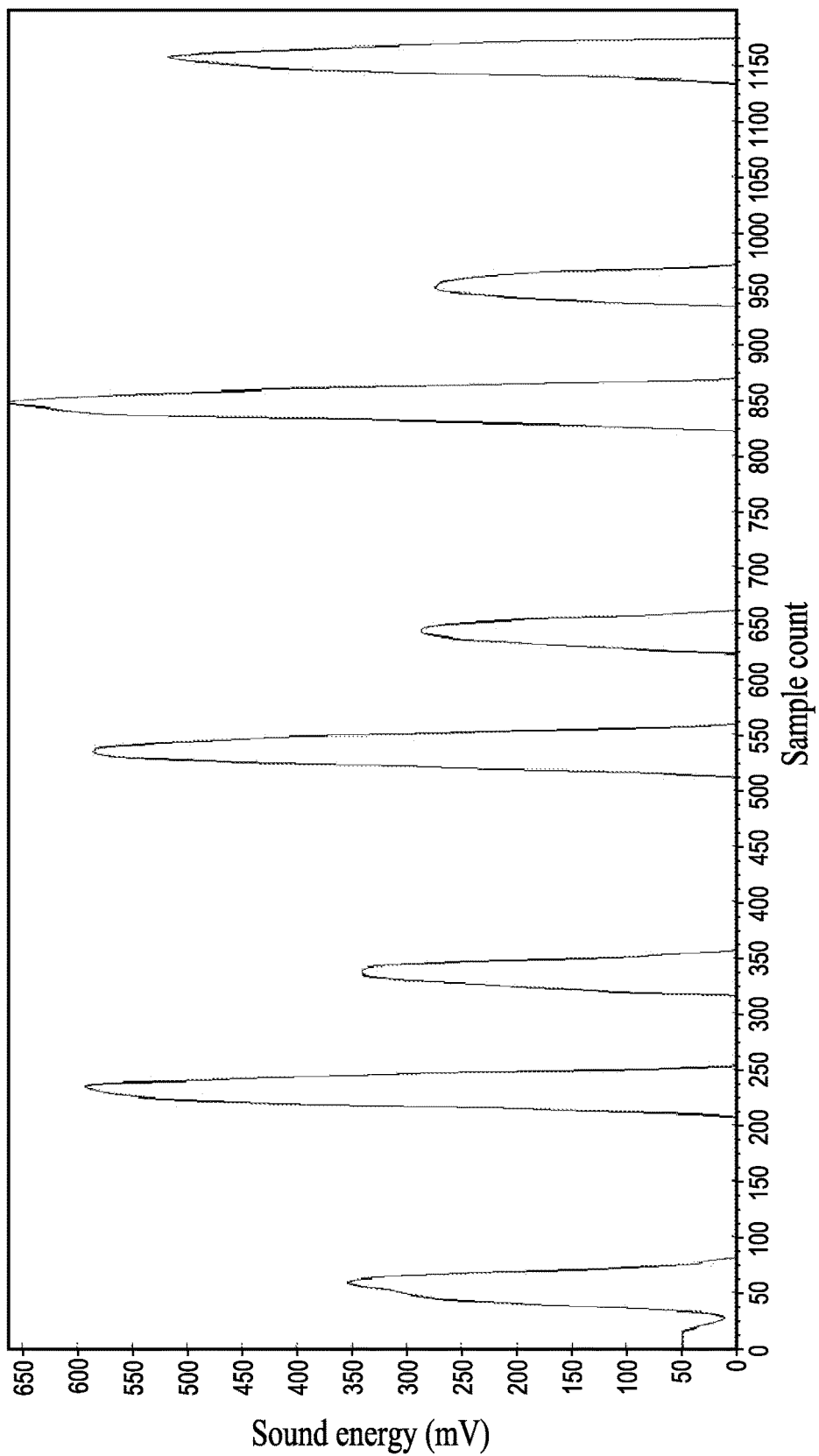
FIG. 9 is a curve diagram of heart sound signals done by a TT SMA filtering process in FIG. 3.

Step S302: Down-sampling step. Specifically, perform a down sampling processing on the initial samples of heart sound signal. The down sampling processing serves to extend a time interval between each adjacent two of the initial samples of heart sound signal and the effect is to reduce the number of the initial samples, so as to speed up computation for heart rate using less samples. With reference to FIG. 5, after the down sampling processing, the first sampling frequency 48 kHz is dropped to a second sampling frequency 375 Hz, which is $1/128$ of the first sampling frequency. When the number of the initial samples sampled per second is 51,200 samples, with reference to FIG. 5, this number can be greatly reduced to the 400 samples, which corresponds to half of the samples in a two-second period. After the down-sampling step is done, the heart rate detection method calculates heart rate every second on a real-time basis using the samples in each second and the samples in a previous second. With reference to FIG. 6, when calculating heart rate at each second, there is no sufficient samples available for calculation of heart rate at the initial two seconds because of the number of minimum samples required for calculation of heart rate at each second is 1,200 while the number of samples acquired at each second is 400. Therefore, the first heart rate calculated is available at the third second because the number of accumulated samples for the first three seconds reaches 1,200. The heart rate at and after the fourth second can be repeatedly calculated by using the 400 samples at the instant second and the 800 samples at the two seconds right before the instant second. Heart rate at each second as shown in FIGS. 7-9 is calculated with 1,200 samples, such that the calculated heart can range from 20 to 220 beat per second.

Step S303 (Bandpass filtering step): Apply a bandpass filter and configure two frequency thresholds to filter out noises falling out of frequency ranges of the first heart sound and the second heart sound, namely, frequency ranges blow 20 Hz and above 100 Hz, from the samples in the two-second period. As noticed from FIG. 7, after the bandpass filtering step is done, samples in corrugated portions other than peak portions are not as dense as those before the bandpass filtering step.

Step S304 (Time sequence (TT) defined filtering step): Acquire absolute values of energy of the samples in the two-second period processed by the bandpass filtering step, take an average energy value for all the samples in the two-second period, configure an energy threshold $\lambda$ from the average energy value, and set energy of the samples below the energy threshold $\lambda$ to be zero. With reference to FIG. 8, the energy threshold $\lambda$ is set to be 0.91e where e is the average energy value of all the samples. Thus, samples with primary energy of heart sound signal and regularity can be found while relatively low-energy noises can be screened out.

Step S305 (TT SMA filtering step): Apply a simple moving average (SMA) filter to continuously redraw each 31 continuous samples identified in the TT defined filtering step with an average energy value of the 31 continuous samples to smoothen or filter out the samples having rough edges, complicated peak energy values and high frequency in FIG. 8, so as to generate the samples in the form of continuous peaks with and smooth contour as shown in FIG. 9. Then, computer algorithm can easily discriminate true peaks from false peaks having rough edges or complicated peak energy values and identify the true peaks for computation of heart rate.

Step S306 (Peak-locating step): Search peaks with maximal energy value in every fixed time duration, apply a heart rate requirement for peak grouping and analysis of a peak-to-peak cycle, and repeatedly identify the peaks corresponding to the first heart sound (S1) and the second heart sound (S2) to calculate the corresponding heart rate.

Step S302 to Step S306 can be grouped to correspond to a heart sound identification and heart rate detection process.

To benchmark performance associated with the measurements of heart rate done by the foregoing heart rate detection method with that done by another PCG-type heart rate detector and compare correlation between measurements of heart rate done by the foregoing heart rate detection method and a typical ECG-type physiological monitor with correlation between measurements of heart rate done by the PCG-type heart rate detector and the typical ECG-type a typical ECG-type physiological monitor, an experiment is set up as follows.

A prototype heart sound acquisition device DS301 built in with the foregoing heart rate detection method and a processor of DS301 performs the heart rate detection method, another PCG-type heart rate detector from 3M® and the physiological monitor Philips® IntelliVue MP70 are used to determine the respective time to successfully determine heart rate for the first time (speed-sec) at five different auscultation positions, that is, the auscultation position for the mitral valve, the auscultation position for the pulmonary valve, the first auscultation position for aortic valve (right aortic position), the second auscultation position for aortic valve (left aortic position), and the auscultation position for tricuspid valve, of a same testee and the heart rate calculated by DS301, 3M® detector and MP70 are recorded and a stopwatch is used to record the time for calculating heart rate for the first time determined by each of DS301, 3M® detector and MP70. Totally, there are 19 testees and 150 test records. Among the 19 testees, 12 testees are repeatedly sampled.

To ascertain whether data collected from the experiment are meaningful and convincible, the heart rate detection method further includes a statistical approach as follows.

Step 307 (Hear rate standard deviation step): Add up the time for calculating heart rate for the first time measured by each of MP70, DS301 and 3M® detector repeatedly from each of the five auscultation positions to take an arithmetic average value of the accumulated time. According to the comparison of the arithmetic average values, which one of DS301 and 3M® detector is quicker in calculating heart rate from each of the five auscultation positions has better performance in terms of the speed of calculating heart rate. Add up a difference between the time for calculating heart rate from each auscultation position for the first time measured by DS301 and MP70 and a difference between the time for calculating heart rate from each auscultation position for the first time measured by MP70 and 3M® detector to take an arithmetic average of each of the accumulated differences in generation of a mean error, which represents a mean error of the time measurements for the auscultation position done by DS301 or 3M® detector. Furthermore, apply standard deviation to the mean error to obtain a standard deviation error representing the degree of stability of the time measurements at the auscultation position done by DS301 or 3M® detector. The arithmetic values and standard deviation errors of DS301 and 3M® detector can be compared to give respective performance indication about heart rate detection at each auscultation position.

Data associated with heart rate calculated by MP70, DS301 and 3M® detector from entire auscultation positions and each auscultation position are used to plot and obtain a coefficient of determination $R^2$ for understanding correlation or similarity between heart rate calculated by DS301 and MP70 and between heart rate calculated by 3M® detector and MP70. Higher coefficient of determination $R^2$ means higher correlation.

Step 308 (TT algorithm output step): Apply a Bland-Altman difference plot serving to assess the consistency between two types of data to be analyzed, and a coefficient of determination and a Pearson's correlation coefficient to determine correlation between heart rate calculated by DS301 and MP70 and between heart rate calculated by 3M® detector and MP70. As high correlation does not necessarily lead to high consistency, the Bland-Altman difference plot is performed first to observe distribution of the residual, which is effective in determining the degree of consistency. Then, the coefficient of determination and the Pearson's correlation coefficient are used to determine the degree of correlation.

The experiment results acquired according to the five auscultation positions are given as follows.

Figure 10A:
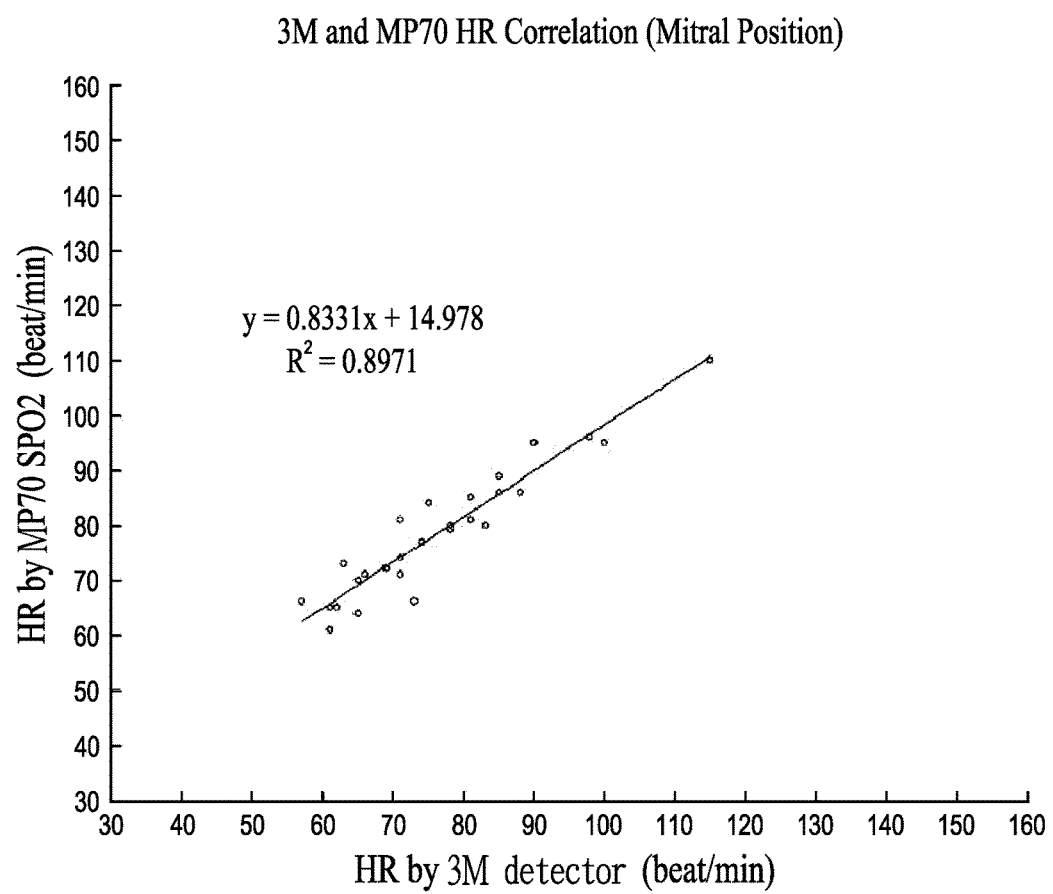
FIG. 10A is a chart illustrating coefficient of determination between heart rate at the mitral position calculated by MP70 and that calculated by 3M detector.
Figure 10B:
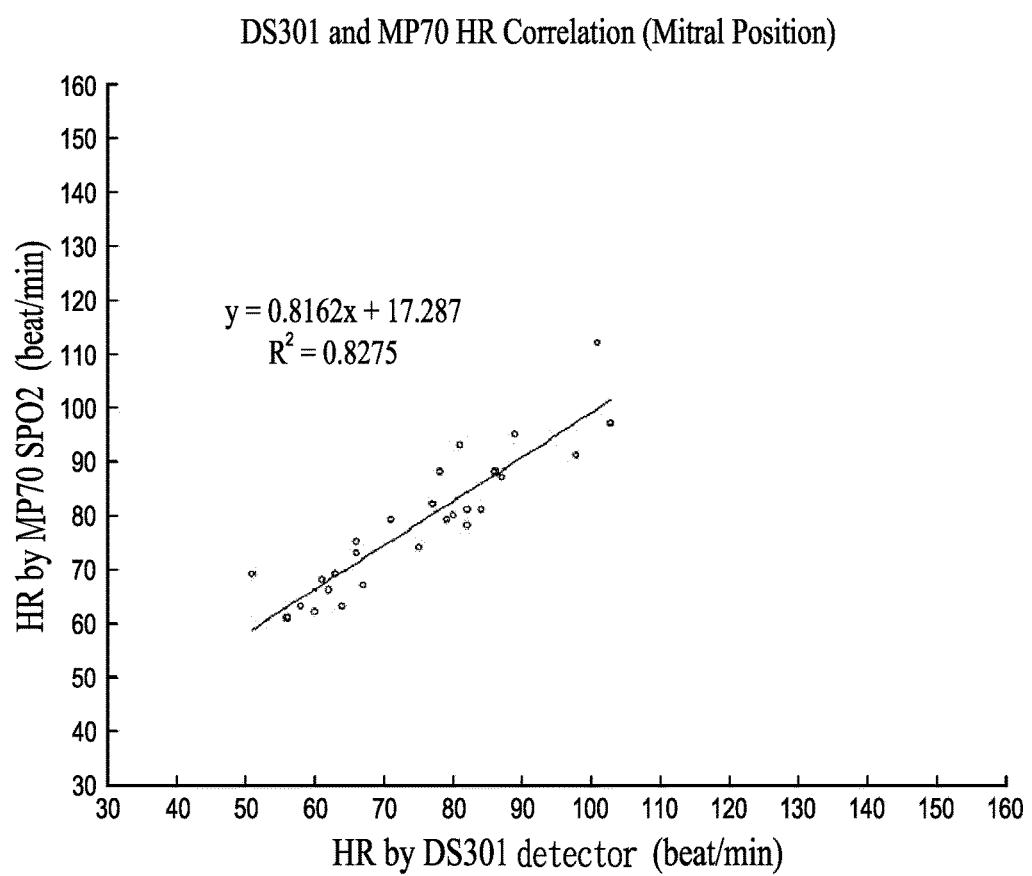
FIG. 10B is a chart illustrating coefficient of determination between heart rate at the mitral position calculated by MP70 and that calculated by the method in FIG. 3.

The following table shows experiment results measured at mitral valve for performance comparison between DS301 and 3M® detector, and FIGS. 10A, 10B respectively employs the coefficient of determination $R^2$ and the Bland-Altman difference plot to respectively compare correlation of heart rate calculated by DS301 and MP70 and correlation of heart rate calculated by 3M® detector and MP70 at mitral valve.

TABLE 1

| Mitral Position | | | | | |
|---|---|---|---|---|---|
| 3M ® detector | | | DS301 | | |
| STDEV ERROR | MEAN ERROR | SPEED (sec) | STDEV ERROR | MEAN ERROR | SPEED (sec) |
| 4.394354 | 2.103448 | 8.55517241 | 5.756983 | 3.571429 | 6.9 |

Figure 11A:
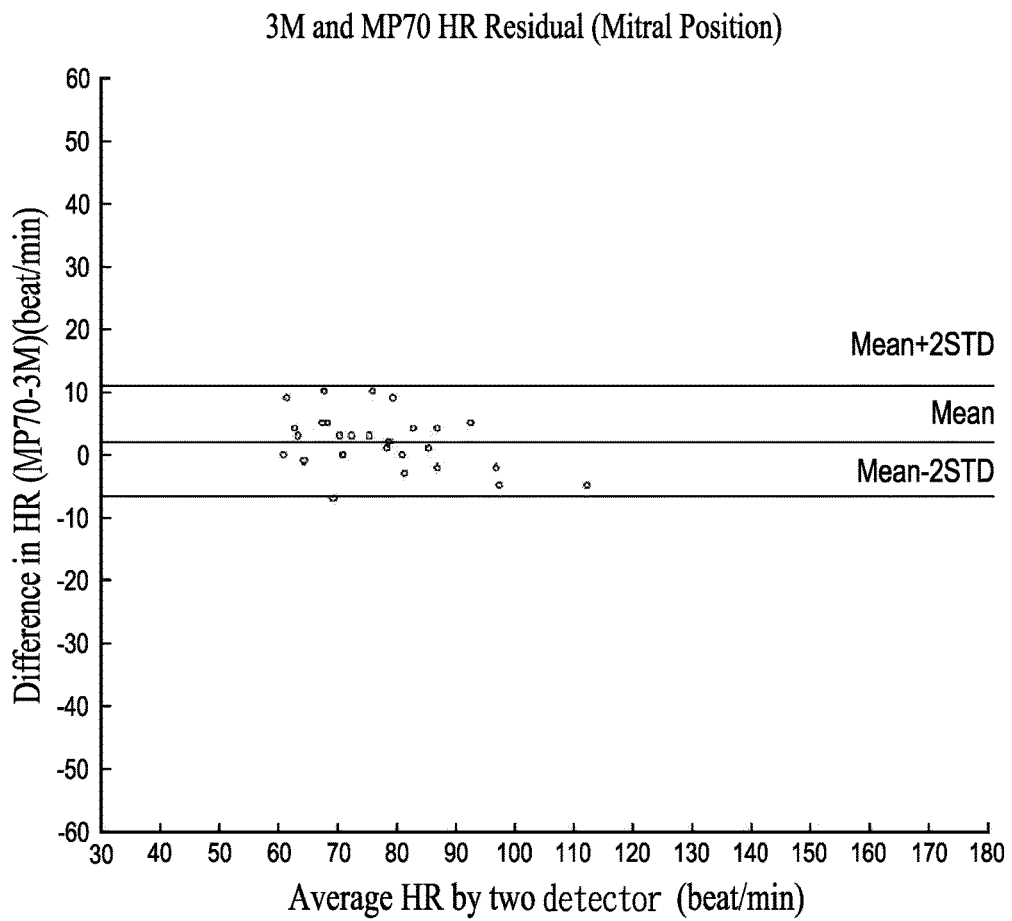
FIG. 11A is a chart illustrating Bland-Altman difference plot between heart rate at the mitral position calculated by MP70 and that calculated by 3M detector.
Figure 11B:
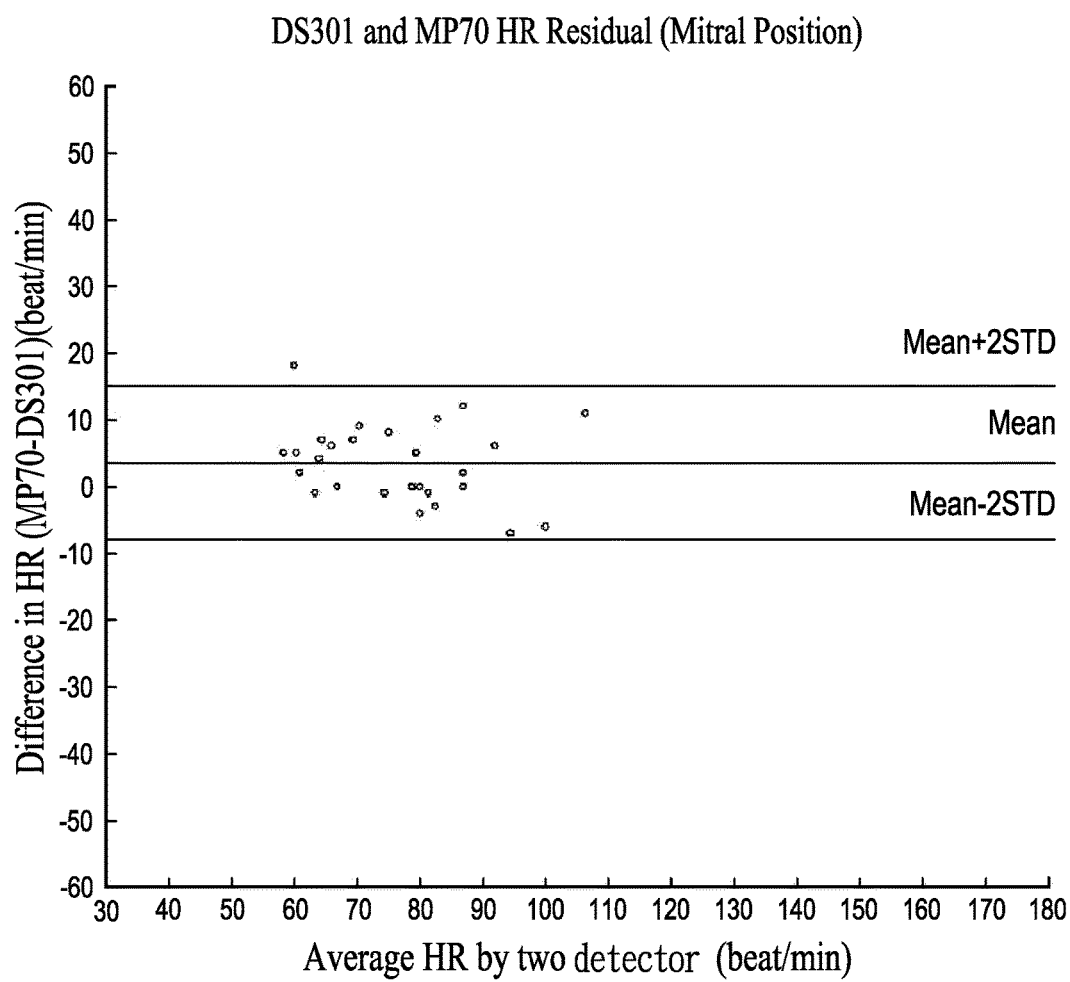
FIG. 11B is a chart illustrating Bland-Altman difference plot between heart rate at the mitral position calculated by MP70 and that calculated by the method in FIG. 3.
Figure 12A:
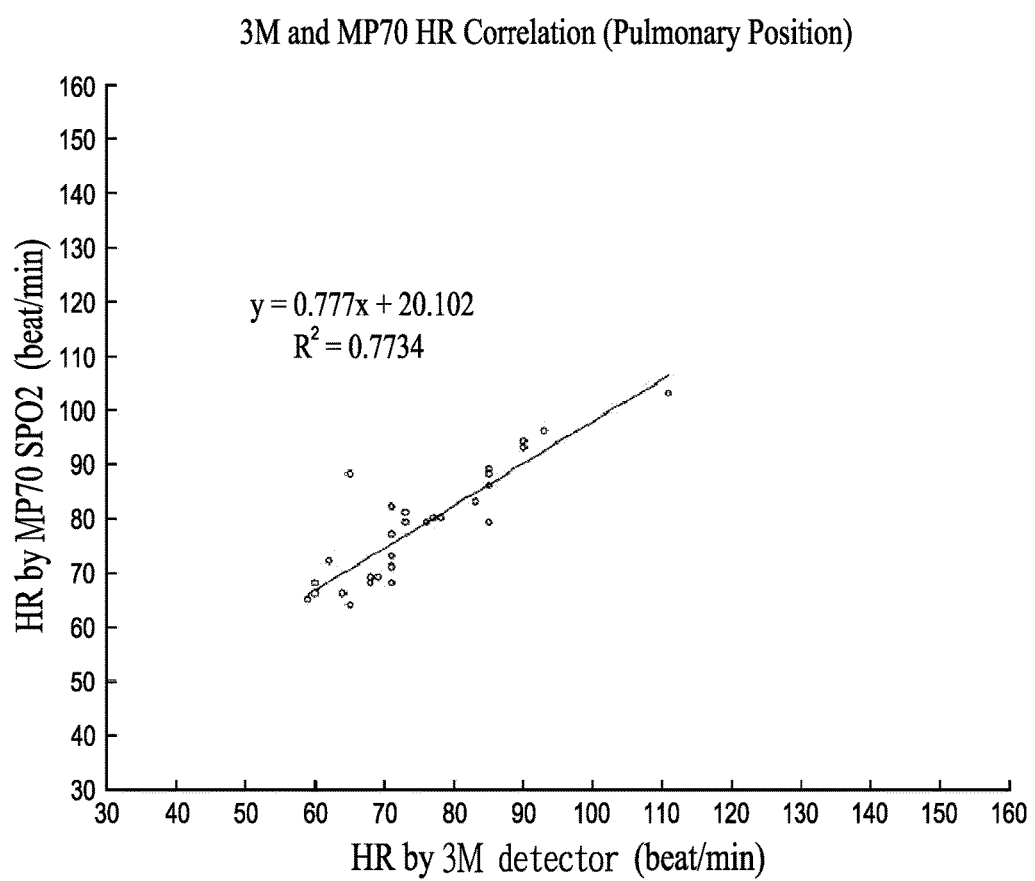
FIG. 12A is a chart illustrating coefficient of determination between heart rate at the pulmonary position calculated by MP70 and that calculated by 3M detector.
Figure 12B:
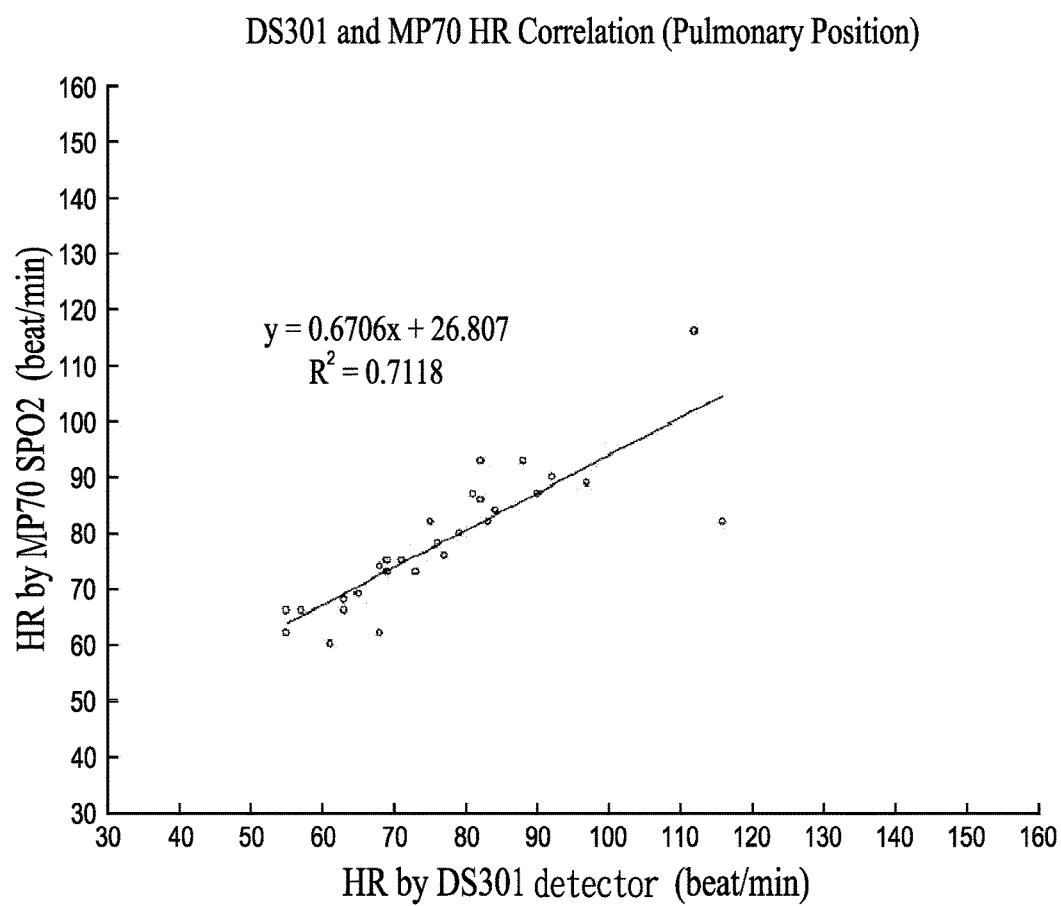
FIG. 12B is a chart illustrating coefficient of determination between heart rate at the pulmonary position calculated by MP70 and that calculated by the method in FIG. 3.

The following table shows experiment results measured at pulmonary valve for performance comparison between DS301 and 3M® detector, and FIGS. 11A, 11B respectively employ the coefficient of determination $R^2$ and the Bland-Altman difference plot to respectively compare correlation of heart rate calculated by DS301 and MP70 and correlation of heart rate calculated by 3M® detector and MP70 at pulmonary valve.

TABLE 2

| Pulmonary Position | | | | | |
|---|---|---|---|---|---|
| 3M ® detector | | | DS301 | | |
| STDEV ERROR | MEAN ERROR | SPEED (sec) | STDEV ERROR | MEAN ERROR | SPEED (sec) |
| 5.664904 | 5.664904 | 5.66490362 | 8.217037 | 1.655172 | 6.63103448 |

Figure 13A:
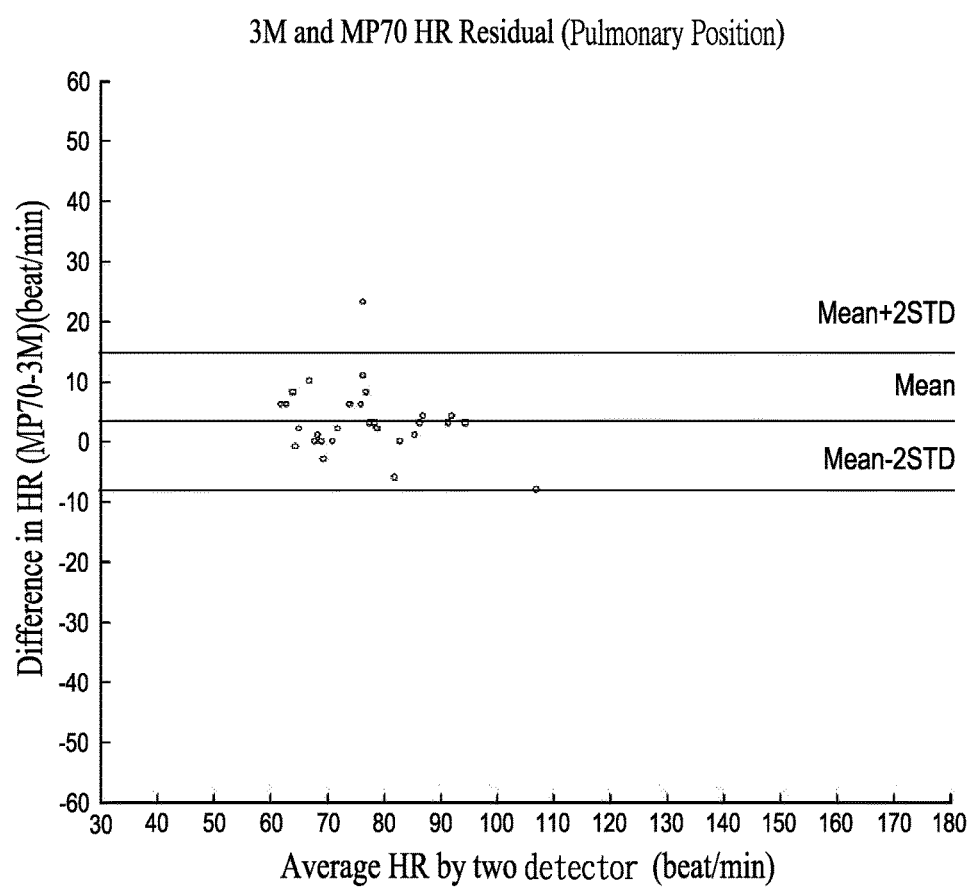
FIG. 13A is a chart illustrating Bland-Altman difference plot between heart rate at the pulmonary position calculated by MP70 and that calculated by 3M detector.
Figure 13B:
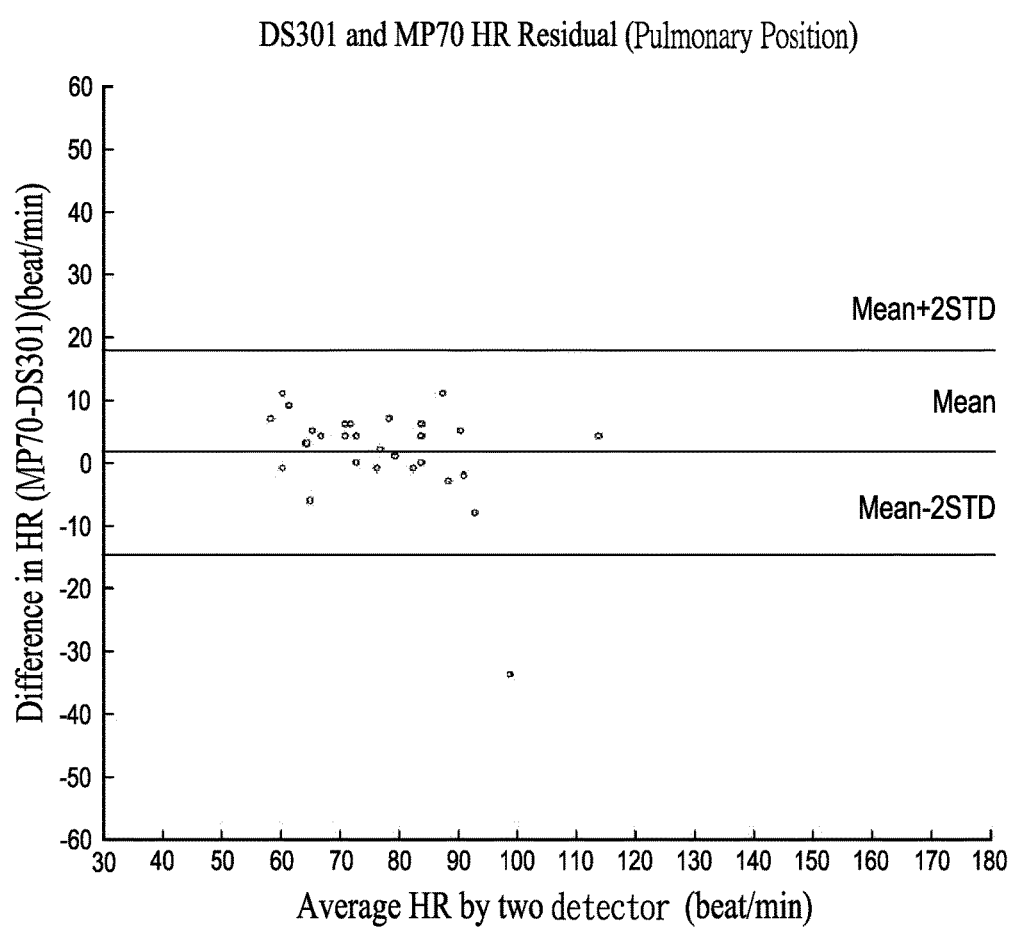
FIG. 13B is a chart illustrating Bland-Altman difference plot between heart rate at the pulmonary position calculated by MP70 and that calculated by the method in FIG. 3.
Figure 14A:
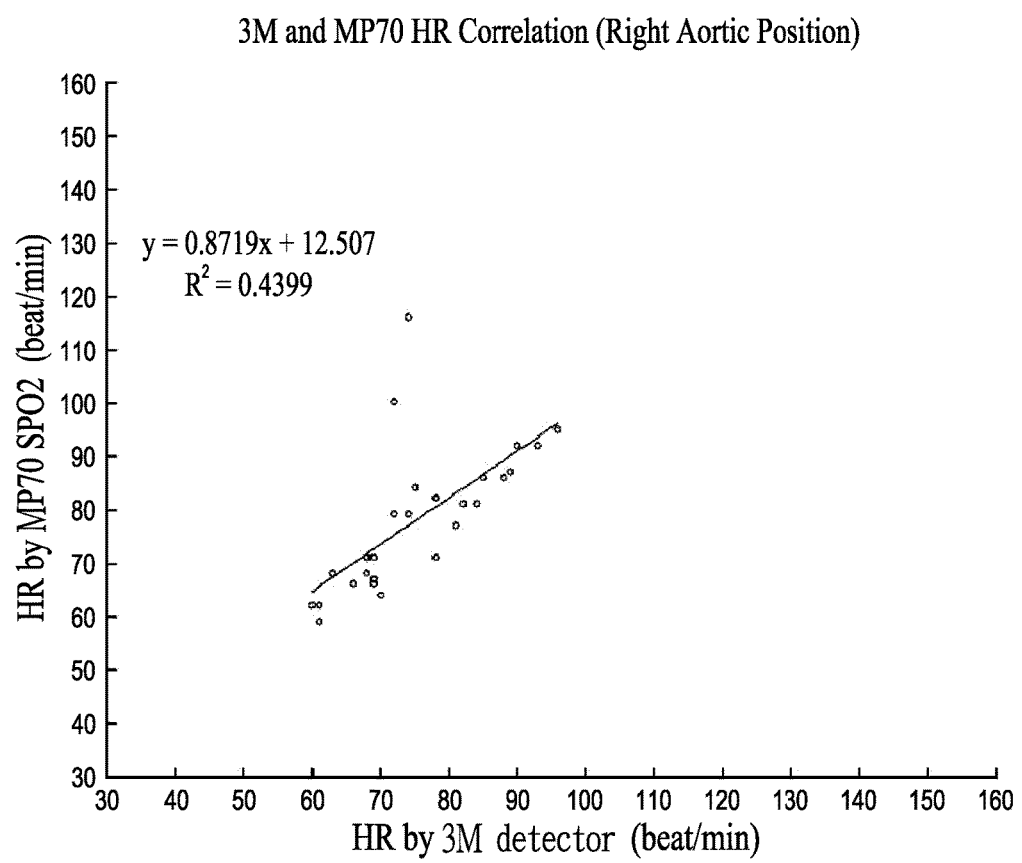
FIG. 14A is a chart illustrating coefficient of determination between heart rate at the right aortic position calculated by MP70 and that calculated by 3M detector.
Figure 14B:
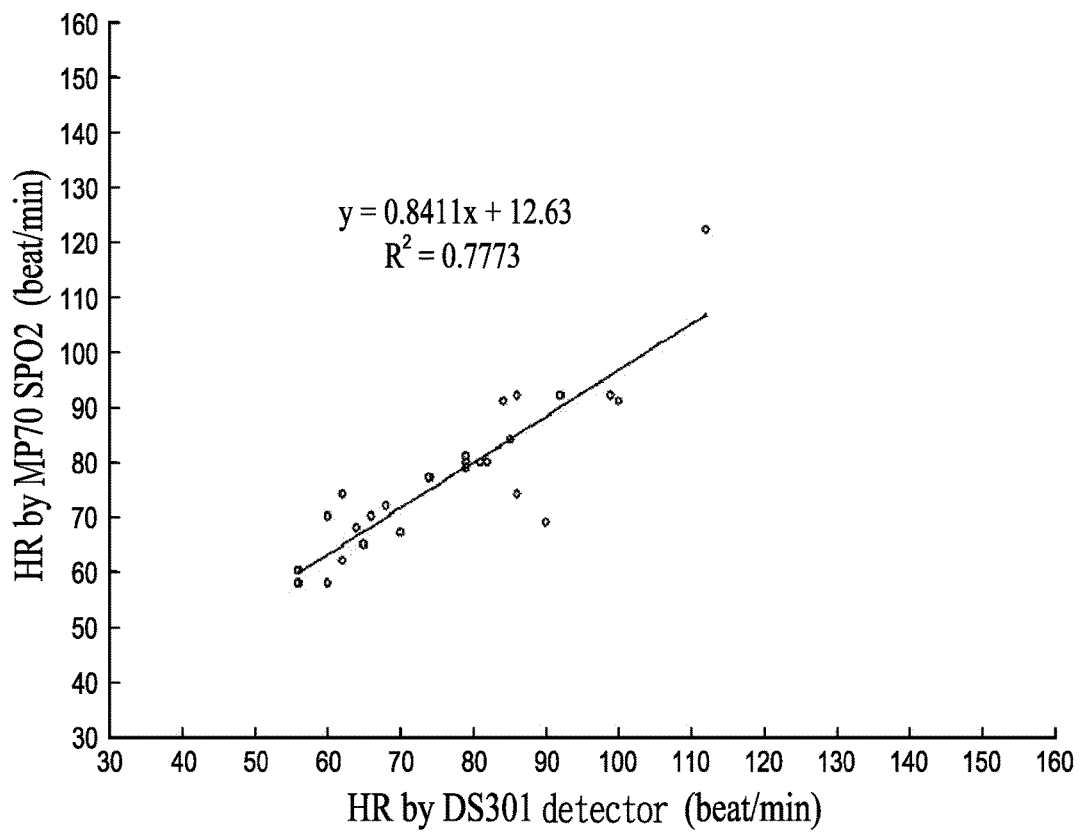
FIG. 14B is a chart illustrating coefficient of determination between heart rate at the right aortic position calculated by MP70 and that calculated by the method in FIG. 3.

The following table shows experiment results measured at aortic valve I for performance comparison between DS301 and 3M® detector, and FIGS. 13A, 13B respectively employ the coefficient of determination $R^2$ and the Bland-Altman difference plot to respectively compare correlation of heart rate calculated by DS301 and MP70 and correlation of heart rate calculated by 3M® detector and MP70 at aortic valve I.

TABLE 3

| Right Aortic Position | | | | | |
|---|---|---|---|---|---|
| 3M ® detector | | | DS301 | | |
| STDEV ERROR | MEAN ERROR | SPEED (sec) | STDEV ERROR | MEAN ERROR | SPEED (sec) |
| 10.16292 | 2.851852 | 11.5925926 | 7.04371 | 0.423077 | 8.04230769 |

Figure 15A:
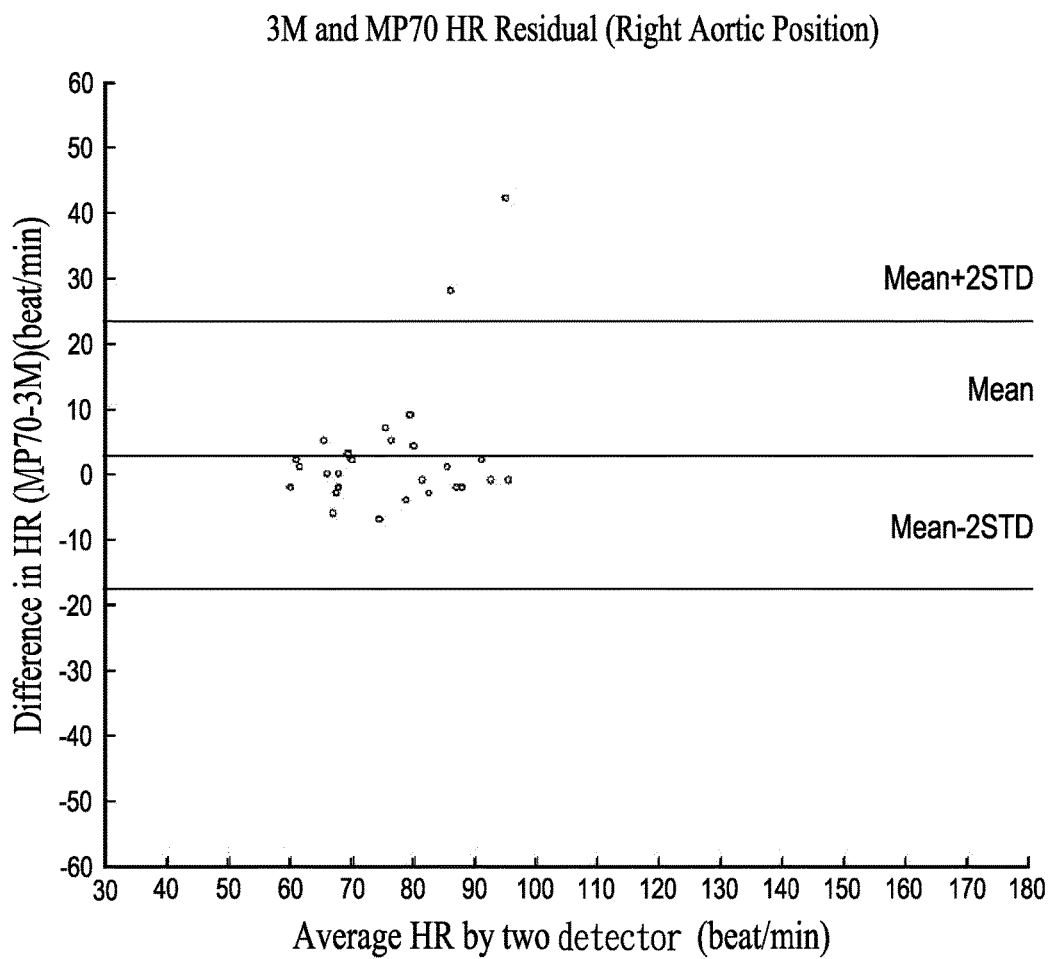
FIG. 15A is a chart illustrating coefficient of determination plot between heart rate at the right aortic position calculated by MP70 and that calculated by 3M detector.
Figure 15B:
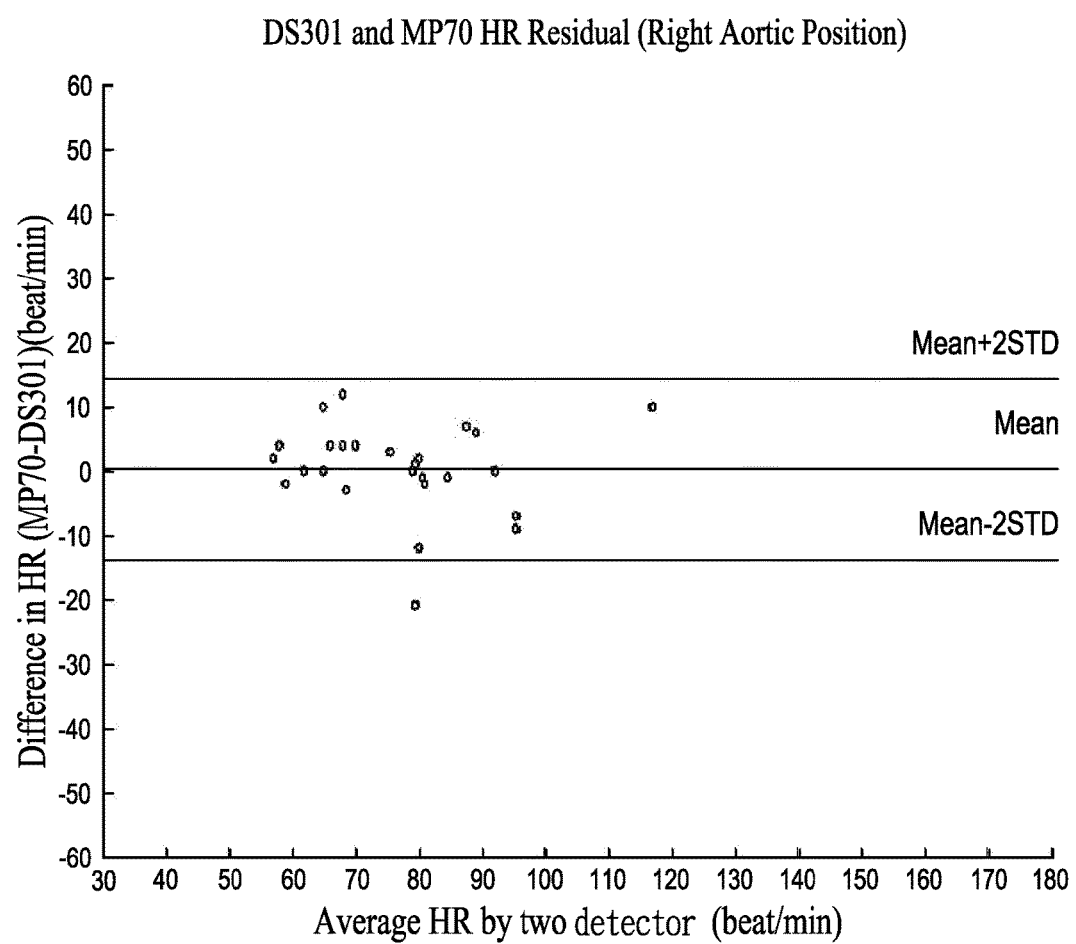
FIG. 15B is a chart illustrating Bland-Altman difference plot between heart rate at the right aortic position calculated by MP70 and that calculated by the method in FIG. 3.
Figure 16A:
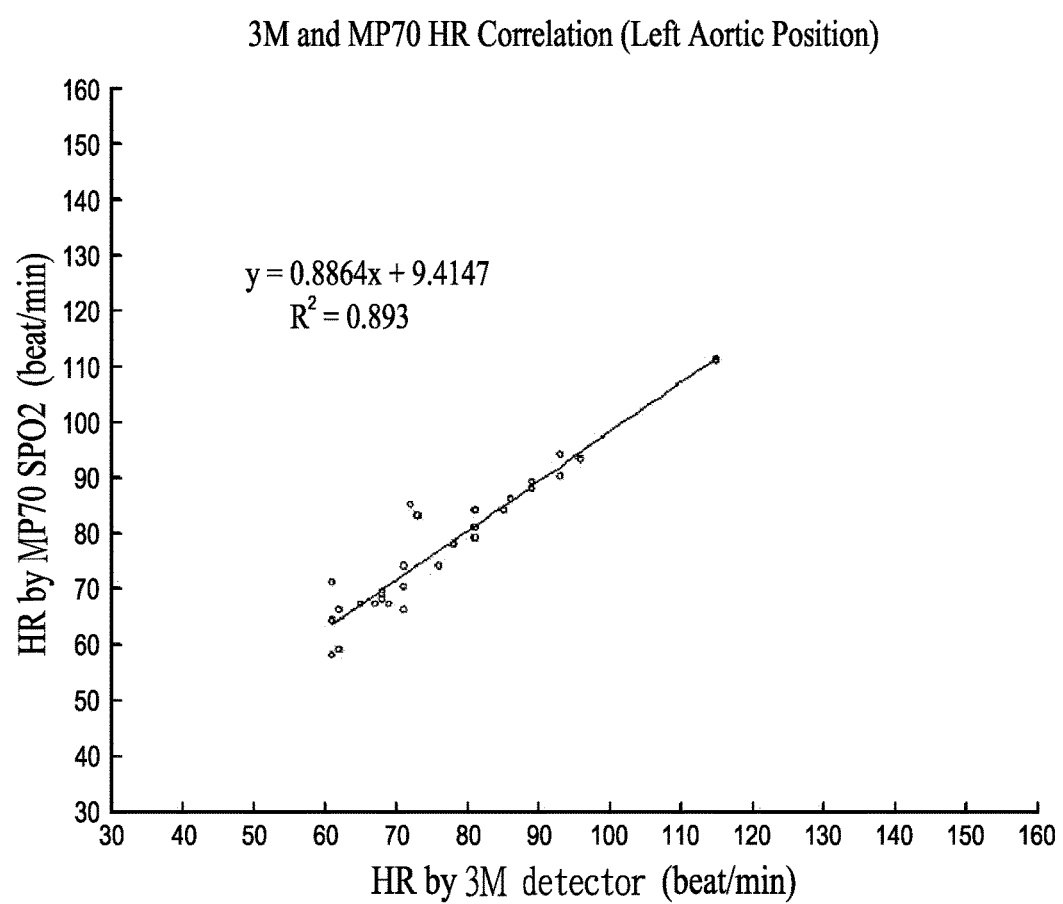
FIG. 16A is a chart illustrating coefficient of determination between heart rate at the left aortic position calculated by MP70 and that calculated by 3M detector.
Figure 16B:
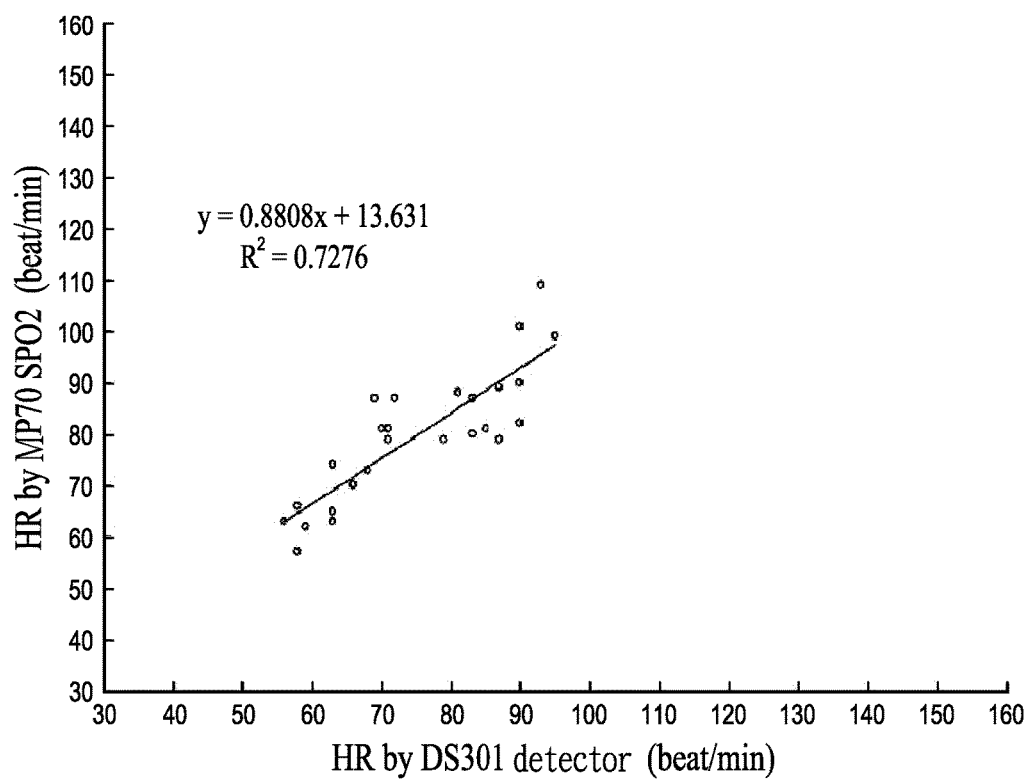
FIG. 16B is a chart illustrating coefficient of determination between heart rate at the left aortic position calculated by MP70 and that calculated by the method in FIG. 3.

The following table shows experiment results measured at aortic valve II for performance comparison between DS301 and 3M® detector, and FIGS. 15A, 15B respectively employ the coefficient of determination $R^2$ and the Bland-Altman difference plot to respectively compare correlation of heart rate calculated by DS301 and MP70 and correlation of heart rate calculated by 3M® detector and MP70 at aortic valve II.

TABLE 4

| Left Aortic Position | | | | | |
|---|---|---|---|---|---|
| 3M ® detector | | | DS301 | | |
| STDEV ERROR | MEAN ERROR | SPEED (sec) | STDEV ERROR | MEAN ERROR | SPEED (sec) |
| 4.284832 | 0.714286 | 7.90714286 | 6.827997 | 4.692308 | 7.18076923 |

Figure 17A:
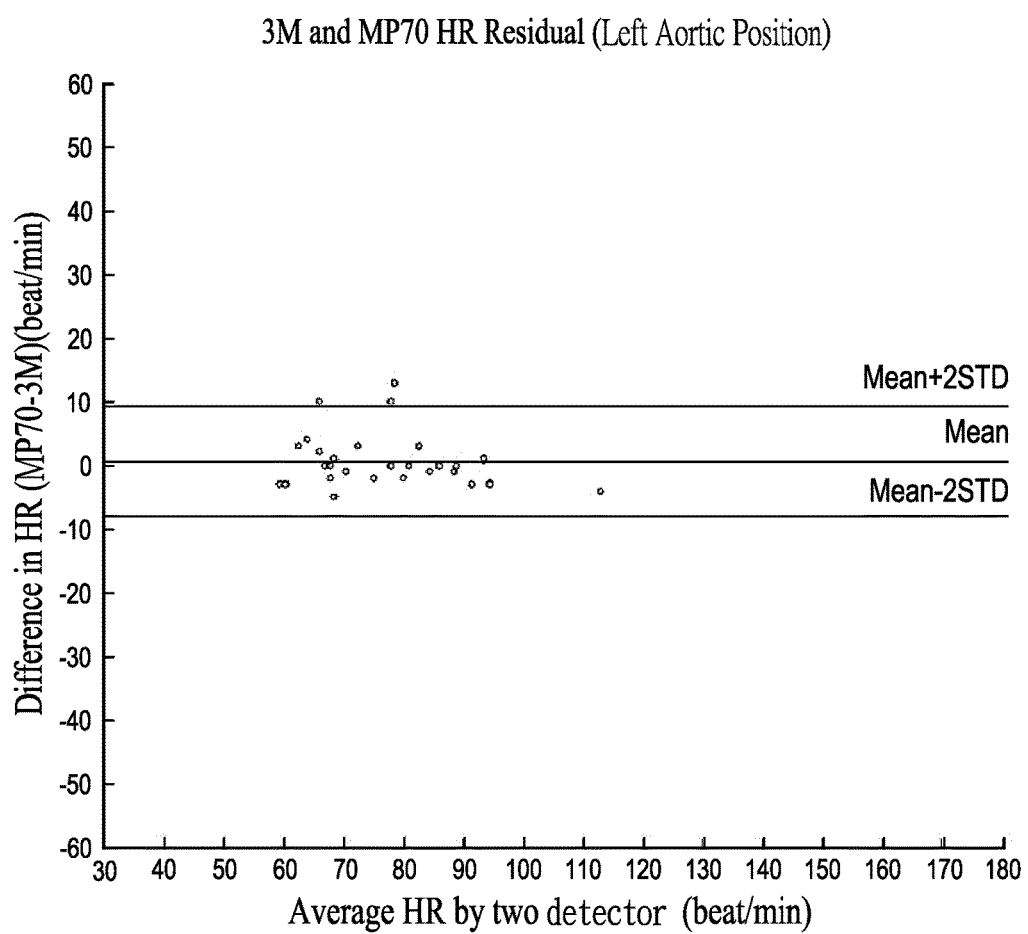
FIG. 17A is a chart illustrating Bland-Altman difference plot between heart rate at the left aortic position calculated by MP70 and that calculated by 3M detector.
Figure 17B:
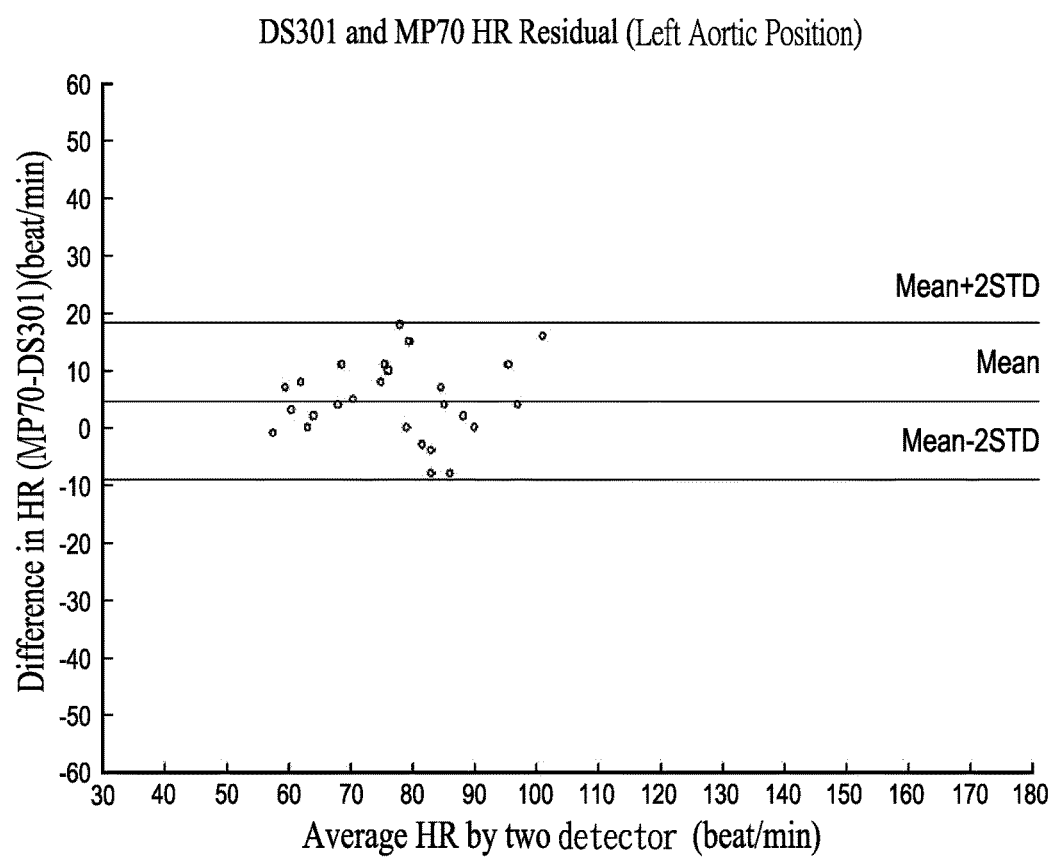
FIG. 17B is a chart illustrating Bland-Altman difference plot between heart rate at the left aortic position calculated by MP70 and that calculated by the method in FIG. 3.
Figure 18A:
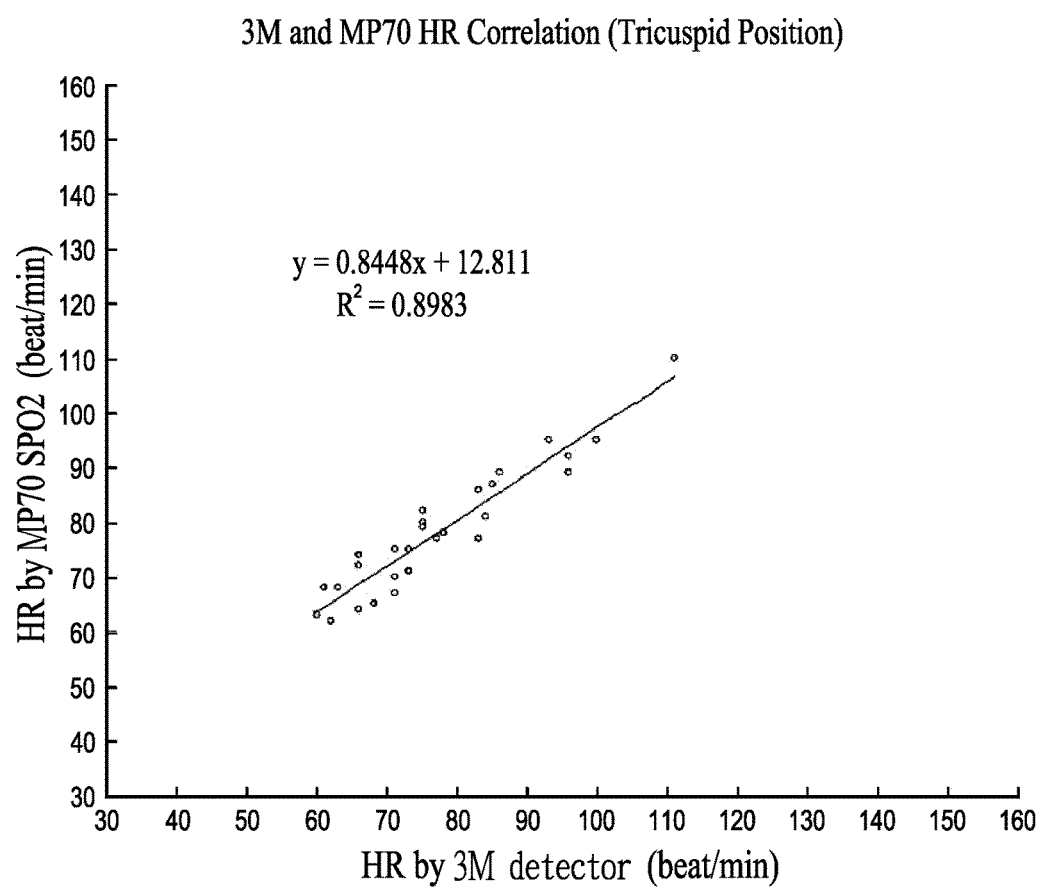
FIG. 18A is a chart illustrating coefficient of determination between heart rate at the tricuspid position calculated by MP70 and that calculated by 3M detector.
Figure 18B:
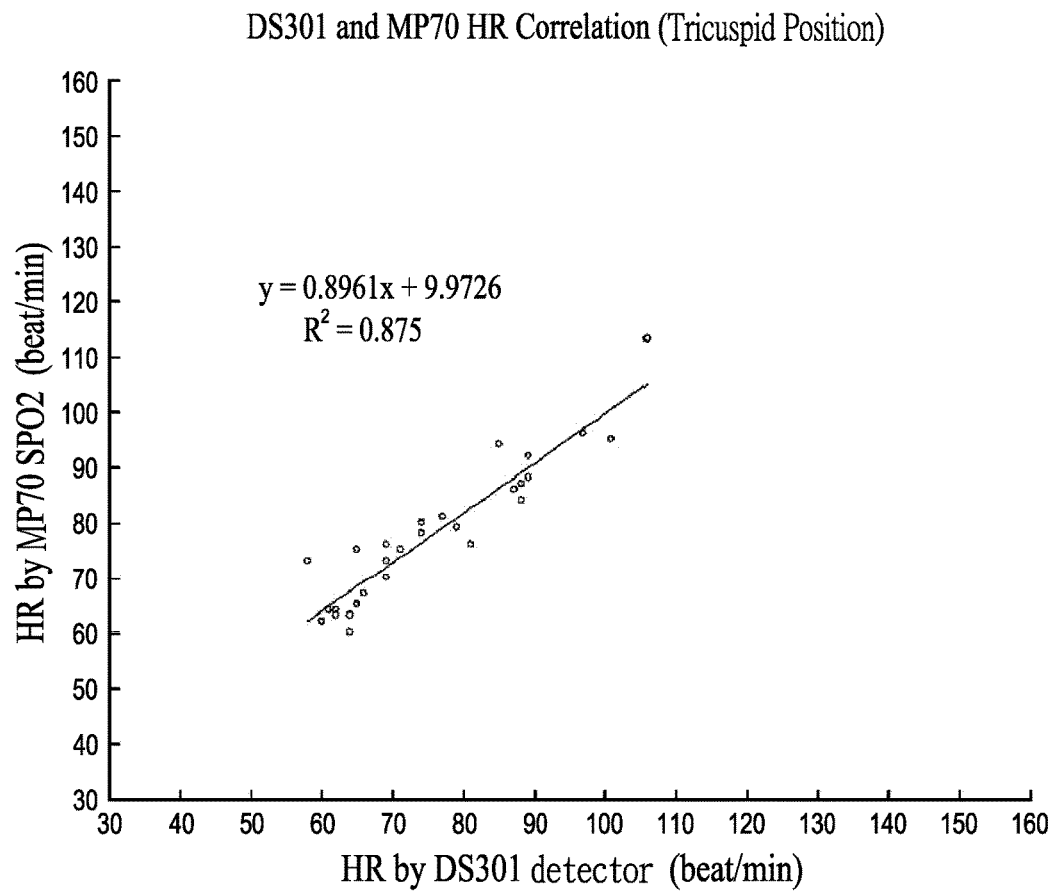
FIG. 18B is a chart illustrating coefficient of determination between heart rate at the tricuspid position calculated by MP70 and that calculated by the method in FIG. 3.

The following table shows experiment results measured at tricuspid valve for performance comparison between DS301 and 3M® detector, and FIGS. 17A, 17B respectively employ the coefficient of determination $R^2$ and the Bland-Altman difference plot to respectively compare correlation of heart rate calculated by DS301 and MP70 and correlation of heart rate calculated by 3M® detector and MP70 at tricuspid valve.

TABLE 5

| Tricuspid Position | | | | | |
|---|---|---|---|---|---|
| 3M ® detector | | | DS301 | | |
| STDEV ERROR | MEAN ERROR | SPEED (sec) | STDEV ERROR | MEAN ERROR | SPEED (sec) |
| 4.100342 | 0.793103 | 9.57931034 | 4.740209 | 2.107143 | 6.46785714 |

Figure 19A:
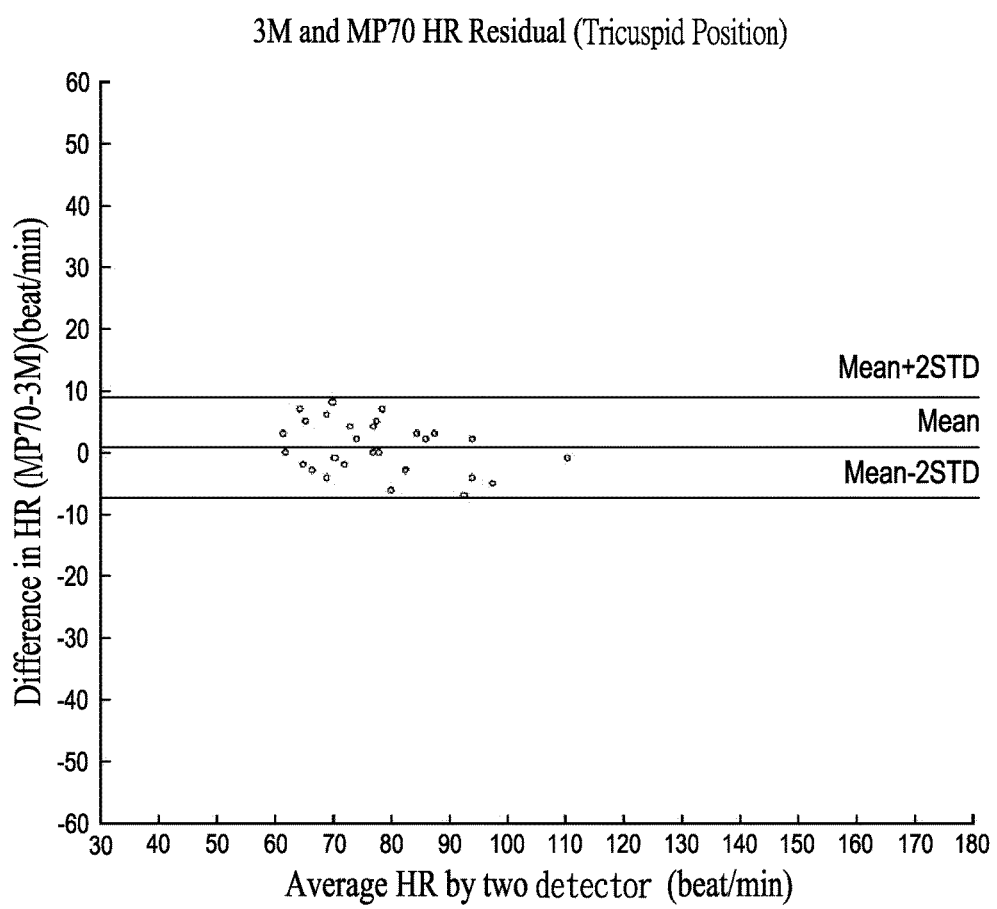
FIG. 19A is a chart illustrating Bland-Altman difference plot between heart rate at the tricuspid position calculated by MP70 and that calculated by 3M detector.
Figure 19B:
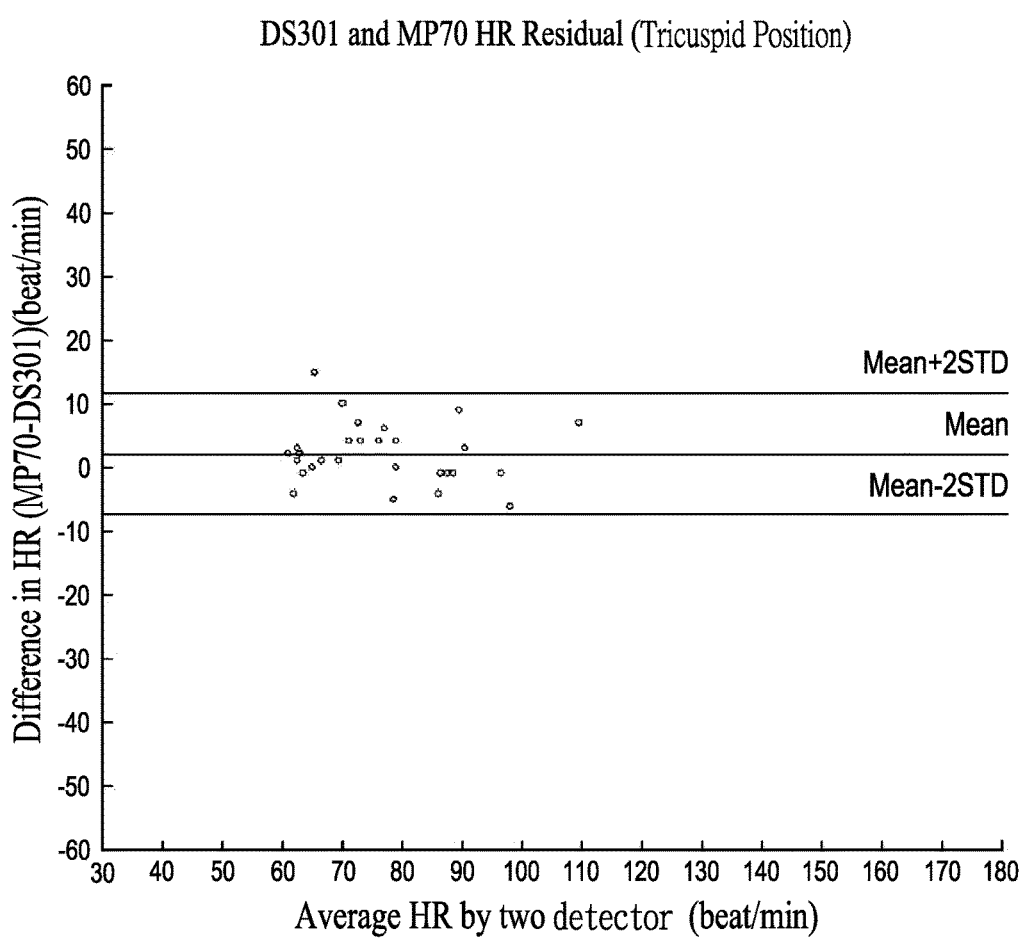
FIG. 19B is a chart illustrating Bland-Altman difference plot between heart rate at the tricuspid position calculated by MP70 and that calculated by the method in FIG. 3.
Figure 20A:
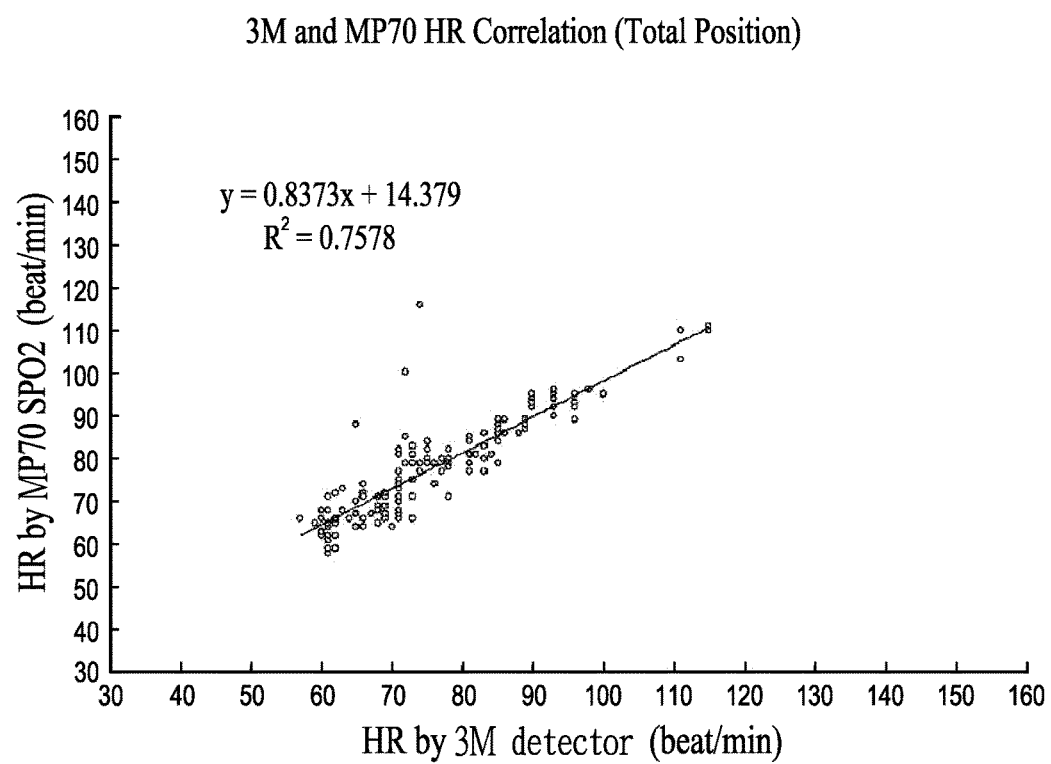
FIG. 20A is a chart illustrating coefficient of determination between heart rate at all the five auscultation positions calculated by MP70 and that calculated by 3M detector.
Figure 20B:
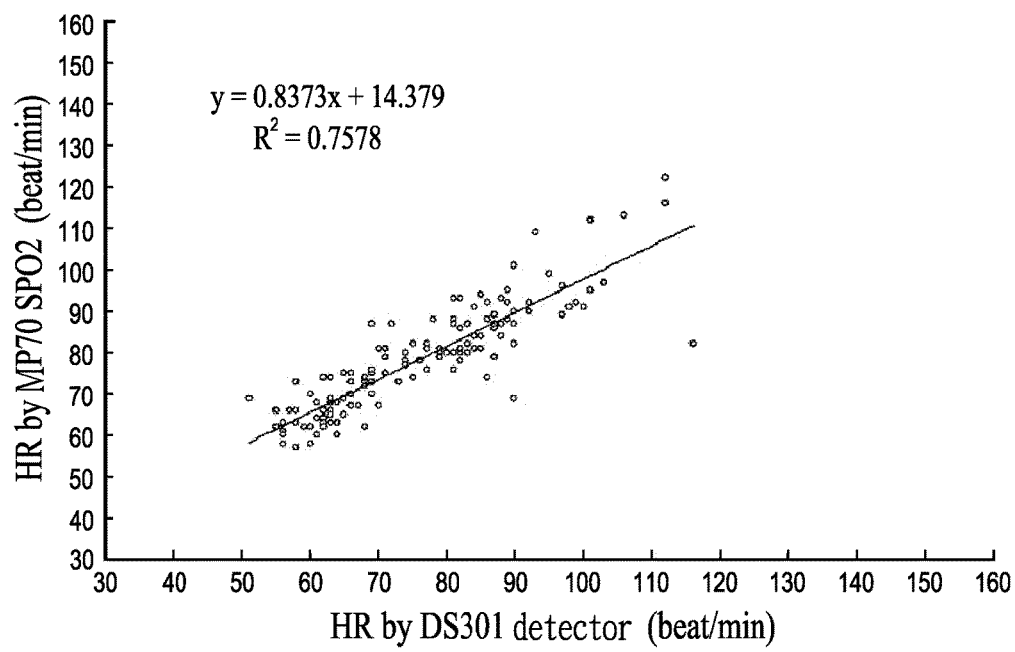
FIG. 20B is a chart illustrating coefficient of determination between heart rate at all the five auscultation positions calculated by MP70 and that calculated by the method in FIG. 3.
Figure 21A:
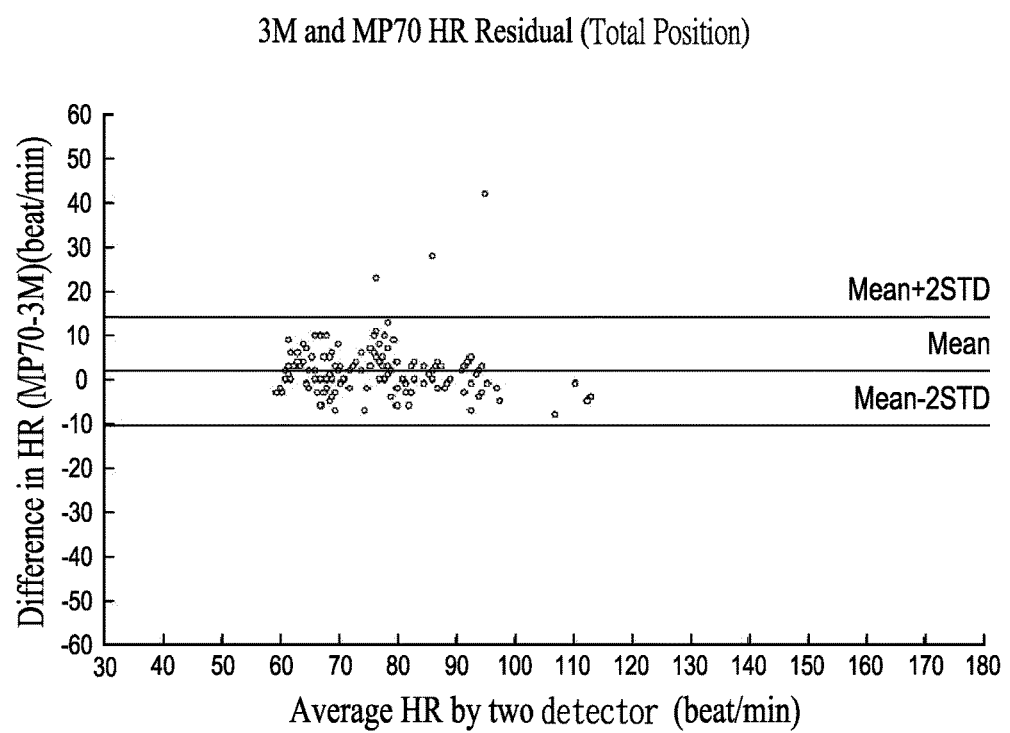
FIG. 21A is a chart illustrating Bland-Altman difference plot between heart rate at all the five auscultation positions calculated by MP70 and that calculated by 3M detector.
Figure 21B:
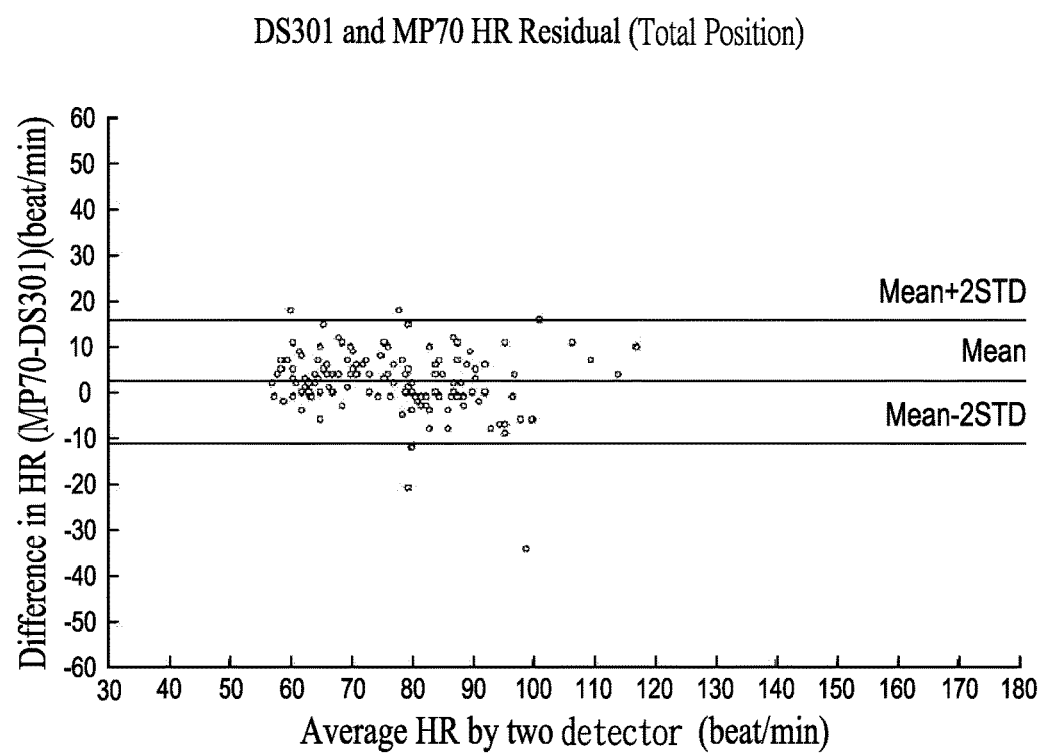
FIG. 21B is a chart illustrating Bland-Altman difference plot between heart rate at all the five auscultation positions calculated by MP70 and that calculated by the method in FIG. 3.

The following table shows performance comparison of the total samples calculated by DS301 and the total samples calculated by 3M® detector, and FIGS. 19A, 19B respectively employ the coefficient of determination $R^2$ and the Bland-Altman difference plot to compare correlation of the total samples of heart rate calculated by DS301 and MP70 and correlation of the total samples of heart rate calculated by 3M® detector and MP70.

TABLE 6

| Total Samples | | | | | |
|---|---|---|---|---|---|
| 3M ® detector | | | DS301 | | |
| STDEV ERROR | MEAN ERROR | SPEED (sec) | STDEV ERROR | MEAN ERROR | SPEED (sec) |
| 10.16292 | 2.851852 | 11.5925926 | 7.04371 | 0.423077 | 8.04230769 |

TABLE 7

| Detection Rate | | | | | |
|---|---|---|---|---|---|
| 3M ® detector | | | DS301 | | |
| Total Sample | Valid Sample | Detection Rate | Total Sample | Valid Sample | Detection Rate |
| 150 | 142 | 94.67% | 150 | 137 | 91.33% |

To sum up and analyze the foregoing information collected from the five auscultation positions, the heart rate measuring speed calculated from any auscultation position by DS301 of the present invention is faster than that calculated by 3M® detector and is 7.025 seconds in average. Among the five auscultation positions, DS301 has the fastest heart rate measuring speed from the tricuspid position (Table 5), which is 6.47 seconds in average while the most stable heart sound signals are from the aortic valve II (Table 4) as the standard deviation error for the left aortic position is approximately 6.83. The mitral position has the second most stable heart sound signals whose standard deviation error is 5.76, and also has a satisfactory heart rate measuring speed at approximately 6.9 seconds. Although the mean error for the right aortic position and the pulmonary position are both low, the standard deviation error for the right aortic position and the pulmonary position are high, meaning that the heart sound signals measured from the right aortic position and the pulmonary position are not stable enough.

With further reference to FIGS. 11B, 13B, 15B, 17B and 19B, a Bland-Altman difference plot is created by taking the average heart beat of MP70 and DS301 as X-axis coordinate, the difference in heart beat between MP70 and DS301 as Y-axis coordinate, the mean error as a reference line parallel to the X axis, and ±two folds of standard deviation error as the 95% confidence interval. As can be seen from FIGS. 11B, 13B, 15B, 17B and 19B, almost all points plotted based on samples of heart rate from all the five auscultation positions fall within the 95% confidence interval, proving that the heart rate values calculated by the DS301 and MP70 have high-degree of consistency.

With further reference to FIGS. 10B, 12B, 14B, 16B and 18B, the values of the coefficient of determination $R^2$ are 0.8275, 0.7118, 0.7773, 0.7276, and 0.875 for the mitral position, pulmonary position, right aortic position, left aortic position, and tricuspid position respectively. According to all the values of the coefficient of determination $R^2$, the correlation between the heart rate calculated by DS301 from the tricuspid position and the mitral position and the reference heart rate calculated by MP70 is higher than that between the heart rate calculated by DS301 from other auscultation positions and the reference heart rate calculated by MP70. Such result can also explain the relatively low standard deviation error of the two auscultation positions.

TABLE 8

| Pearson Correlation for five auscultation positions | | |
|---|---|---|
| Mitral position | Correlation coefficient | 0.91** |
| | Significant (2-tailed) | 0.000 |
| | N | 28 |
| Pulmonary position | Correlation coefficient | 0.844** |
| | Significant (2-tailed) | 0.000 |
| | N | 29 |
| Right aortic position | Correlation coefficient | 0.879** |
| | Significant (2-tailed) | 0.000 |
| | N | 27 |

TABLE 8-continued

Pearson Correlation for five auscultation positions

| | | |
|---|---|---|
| Left aortic position | Correlation coefficient | 0.853** |
| | Significant (2-tailed) | 0.000 |
| | N | 26 |
| Tricuspid position | Correlation coefficient | 0.941** |
| | Significant (2-tailed) | 0.000 |
| | N | 27 |

**Correlation is significant at the 0.01 level (2-tailed)

Table 7 is used to determine Pearson Correlation, which is a measure of the strength of the linear relationship between the heart rate calculated by DS301 at the five auscultation positions and that calculated by MP70. As can be seen from Table 7, the correlation coefficient in the five auscultation positions falls in a range of 0.7~0.99 with a p value less than 0.001. Accordingly, the heart rate calculated by DS301 at the five auscultation positions and that calculated by MP70 are high are highly correlated. In particular, the correlation coefficient for the relationship between heart rate calculated by DS301 from the tricuspid position and that calculated by MP70 reaches a high value 0.941, representing that the readings of heart beat at the tricuspid position calculated by DS301 are more accurate than those at other auscultation positions.

The heart rate detection method in accordance with the present invention can be applied to diagnosis of loss of pulse, ventricular arrhythmia, ventricular tachycardia and ventricular fibrillation.

Figure 22:
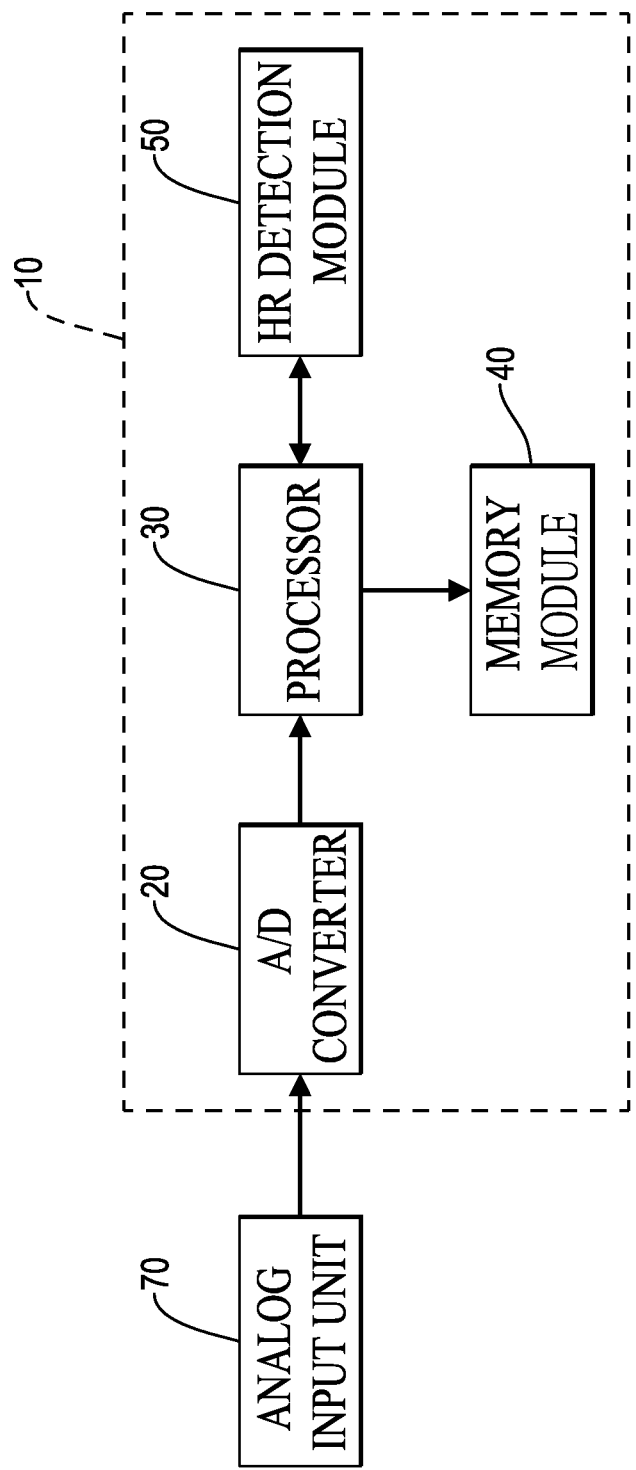
FIG. 22 is a functional block diagram of a heart rate detection device in accordance with the present invention.

With reference to FIG. 22, a heart rate detection device using heart sounds 10 in accordance with the present invention includes an analog-to-digital (A/D) converter 20, a processor 30, a memory module 40 and a heart rate detection module 50. The heart rate detection device 10 is connected to an analog input unit 70. The analog input module receives heart sounds in the form of analog signal measured from the five auscultation positions.

The A/D converter 20 is connected to the analog input unit 70 and converts the heart sounds into digital data. The processor 30 is connected to the A/D converter 20, receives the digital data transmitted from the A/D converter 20. The memory module 40 is connected to the processor 30 and stores the digital signals. The heart rate detection module 50 is connected to the processor 30, receives the digital data transmitted from the processor 30, and performs the down-sampling process, the band-pass filtering process, the TT defined filtering process, the TT SMA filtering process and the peak-locating process as mentioned in the foregoing heart rate detection method to acquire heart rate of each auscultation position.

In sum, the heart rate detection method in accordance with the present invention lowers the quantity of samples of heart sound collected from the five auscultation positions, including the mitral position, the pulmonary position, the right aortic position, the left aortic position, and the tricuspid position, of multiple testees through the down-sampling step, bandpass filtering step, TT defined filtering step, TT SMA filtering step, peak-locating step conducted in an experiment and repeatedly identify the first heart sound and the second heart sound for heart rate detection. The heart rate detection method also effectively lowers the possibility of error in calculating heart rate arising from noises in the surrounding environment. Heart rate data calculated by the heart rate detection method at the five auscultation positions are statistically analyzed by using the standard deviation error, the coefficient of determination, the Bland-Altman difference plot and the Pearson's correlation coefficient to find out that the heart rate detection method has s faster average speed at 7.025 seconds in calculating heart rate than the PCG-type 3M® detector, a detection rate of the heart rate detection method is 91.33%, and the heart rate calculated at the tricuspid position and the mitral position has higher heart rate measuring speed in contrast to the PCG-type 3M® detector and higher degree of correlation with the ECG-type physiological monitor MP70, rendering the heart rate detection method and any heart sound acquisition device built in with the heart rate detection method with competitive edge in field of heart rate detection using heart sound.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A heart rate detection method using heart sounds acquired from auscultation positions, wherein the heart rate detection method is built in a heart rate detection device and is performed by a processor of the heart rate detection device, the heart rate detection method comprising steps of:
repeatedly acquiring and processing samples of heart sound at a first sampling frequency and a second sampling frequency from multiple auscultation positions of multiple testees using a heart sound identification and detection process to identify a first heart sound occurring at beginning of a systole and a second heart sound occurring at beginning of a diastole paired to the systole from the samples wherein the heart sound identification and detection process comprises steps of:
performing a down sampling processing on the samples of heart sound to lower the first sampling frequency down to the second sampling frequency;
performing a band-pass filtering process by a bandpass filter with two frequency thresholds to filter out noises falling out of frequency ranges of the first heart sound and the second heart sound from the samples of heart sound;
performing a time sequence (TT) defined filtering process by acquiring an absolute value of energy of the filtered samples, taking an average energy value of the samples having positive absolute values, configuring an energy threshold from the average energy value, and setting an energy of the samples lower than the energy threshold to zero to obtain multiple continuous samples;
performing a TT simple moving average (SMA) filtering process by a SMA filter to continuously redraw each of the multiple continuous samples to smoothen the filtered samples to generate smoothened samples having continuous peaks with smooth contour; and
performing a peak-locating process by searching the peaks corresponding to each pair of the first heart sound and the second heart sound from the smoothened samples to calculate a corresponding target heart rate; and
calculating the target heart rate for each of the auscultation positions according to each pair of the first heart sound and the second heart sound, and recording a target heart rate detection time for each of the auscultation positions when calculation of the target heart rate for the auscultation position is completed; and calculating a reference heart rate for each of the auscultation position by reference heart rate detector, and recording a reference heart rate detection time for each of the auscultation positions when calculation of the reference heart rate for the auscultation position is completed, wherein the target heart rate detection time, the reference heart rate detection time, the target heart rate and the reference heart rate for each of the auscultation positions are analyzed by a statistical process to obtain an analysis result.

2. The heart rate detection method as claimed in claim 1, wherein the statistical process comprises steps of:

adding up the target heart rate detection time for each of the auscultation positions of all the testees to calculate an arithmetic average value of an accumulated target heart rate detection time as a target heart rate detection speed for the auscultation position;

adding up a difference between the target heart rate detection speed and a reference heart rate detection speed for each of the auscultation positions of all the testees to take an arithmetic average of an accumulated difference as a mean error for the auscultation position;

applying standard deviation to the mean error for each of the auscultation positions to obtain a standard deviation error for the auscultation position representing a degree of stability of the target heart rate for the auscultation position of all the testees, wherein a lower value of the standard deviation error represents a higher degree of stability; and assessing a degree of consistency and a degree of correlation between the target heart rate for each of the auscultation positions of all the testees and the reference heart rate for the auscultation position of all the testees using a Bland-Altman difference plot, a coefficient of determination and a Pearson's correlation coefficient respectively, wherein a higher degree of correlation represents higher accuracy of the target heart rate for a corresponding auscultation position.

3. The heart rate detection method as claimed in claim 1, wherein the multiple auscultation positions comprise an auscultation position for mitral valve, an auscultation position for pulmonary valve, a first auscultation position for aortic valve, a second auscultation position for aortic valve, and an auscultation position for tricuspid valve.

4. The heart rate detection method as claimed in claim 1, wherein in the step of performing a down sampling processing on the samples of heart sound, the target heart rate for each of the auscultation positions of each of the testees per second is calculated by combining the samples of heart sound sampled at a second and the samples of heart sound sampled at two seconds ahead of the second.

5. The heart rate detection method as claimed in claim 1, applied to diagnosis of loss of pulse, ventricular arrhythmia, ventricular tachycardia and ventricular fibrillation.

6. A heart rate detection device connected to an analog input unit receiving heart sounds in the form of analog signal measured from multiple auscultation positions, the heart rate detection device comprising:

an analog-to-digital (A/D) converter adapted to connect to the analog input module and converting the heart sounds into digital data;

a processor connected to the A/D converter, and receiving the digital data transmitted from the A/D converter;

a memory module connected to the processor and storing the digital signals; and a heart rate detection module connected to the processor, receiving the digital data transmitted from the processor, and performing steps of:

performing a heart sound identification and detection process, comprising steps of:

performing a down sampling processing on the samples of heart sound to lower the first sampling frequency down to the second sampling frequency;

performing a band-pass filtering process by a bandpass filter with two frequency thresholds to filter out noises falling out of frequency ranges of the first heart sound and the second heart sound from the samples of heart sound;

performing, a time sequence (TT) defined filtering process by acquiring an absolute value of energy of the filtered samples, taking an average energy value of the samples having positive absolute values, configuring an energy threshold from the average energy value, and setting an energy of the samples lower than the energy threshold to zero to obtain multiple continuous samples;

performing a TT simple moving average (SMA) filtering process by a SMA filter to continuously redraw each of the multiple continuous samples to smoothen the filtered samples to generate smoothened samples having continuous peaks with smooth contour; and performing a peak-locating process by searching the peaks corresponding to each pair of the first heart sound and the second heart sound from the smoothened samples to calculate a corresponding target heart rate; and calculating the target heart rate for each of the auscultation positions according to each pair of the first heart sound and the second heart sound, and recording a target heart rate detection time for each of the auscultation positions when calculation of the target heart rate for the auscultation position is completed; and calculating a reference heart rate for each of the auscultation positions by a reference heart rate detector, and recording a reference heart rate detection time for each of the auscultation positions when calculation of the reference heart rate for the auscultation position is completed, wherein the target heart rate detection time, the reference heart rate detection time, the target heart rate and the reference heart rate for each of the auscultation positions are analyzed by a statistical process to obtain an analysis result.

7. The heart rate detection device as claimed in claim 6, wherein the statistical process comprises steps of:

adding up the target heart rate detection time for each of the auscultation positions of all the testees to calculate an arithmetic average value of an accumulated target heart rate detection time as a target heart rate detection speed for the auscultation position;

adding up a difference between the target heart rate detection speed and the reference heart rate detection speed for each of the auscultation positions of all the testees to take an arithmetic average of an accumulated difference as a mean error for the auscultation position;

applying standard deviation to the mean error for each of the auscultation positions to obtain a standard deviation error for the auscultation position representing a degree of stability of the target heart rate for the auscultation position of all the testees, wherein a lower value of the standard deviation error represents a higher degree of stability; and assessing a degree of consistency and a degree of correlation between the target heart rate for each of the auscultation positions of all the testees and the reference heart rate for the auscultation position of all the testees using a Bland-Altman difference plot, a coefficient of determination and a Pearson's correlation coefficient respectively, wherein a higher degree of correlation represents higher accuracy the target heart rate for a corresponding auscultation position.

8. The heart rate detection device as claimed in claim 6, wherein the multiple auscultation positions comprise an auscultation position for mitral valve, an auscultation position for pulmonary valve, a first auscultation position for aortic valve, a second auscultation position for aortic valve, and an auscultation position for tricuspid valve.

9. The heart rate detection device as claimed in claim 6, wherein in the step of performing a down sampling processing on the samples of heart sound, the target heart rate for each of the auscultation position of each testee per second is calculated by combining the samples of heart sound sampled at a second and the samples of heart sound sampled at two seconds ahead of the second.

10. The heart rate detection device as claimed in claim 6, applied to diagnosis of loss of pulse, ventricular arrhythmia, ventricular tachycardia and ventricular fibrillation.

* * * * *